United States Patent
Scott et al.

(10) Patent No.: US 6,709,464 B2
(45) Date of Patent: Mar. 23, 2004

(54) CROSS-LINKED ULTRA-HIGH MOLECULAR WEIGHT POLYETHYLENE FOR MEDICAL IMPLANT USE

(75) Inventors: Marcus L. Scott, Memphis, TN (US); Shilesh C. Jani, Memphis, TN (US)

(73) Assignee: Smith & Nephew, Inc., Research, Memphis, TN (US)

( * ) Notice: Subject to any disclaimer, the term of this patent is extended or adjusted under 35 U.S.C. 154(b) by 0 days.

(21) Appl. No.: 10/271,859

(22) Filed: Oct. 16, 2002

(65) Prior Publication Data

US 2003/0130743 A1 Jul. 10, 2003

Related U.S. Application Data

(62) Division of application No. 09/792,690, filed on Feb. 23, 2001, now Pat. No. 6,547,828.

(51) Int. Cl.[7] .................................................. A61F 2/34
(52) U.S. Cl. .................................................. 623/23.58
(58) Field of Search ........................... 623/11.11, 16.11, 623/23.58, 23.59

(56) References Cited

U.S. PATENT DOCUMENTS

| | | |
|---|---|---|
| 4,055,862 A | 11/1977 | Farling |
| 4,508,606 A | 4/1985 | Andrade et al. |
| 5,030,402 A | 7/1991 | Zachariades |
| 5,037,928 A | 8/1991 | Li et al. |
| 5,037,938 A | 8/1991 | Brewbaker et al. |
| 5,414,049 A | 5/1995 | Sun et al. |
| 5,449,745 A | 9/1995 | Sun et al. |
| 5,543,471 A | 8/1996 | Sun et al. |
| 5,650,485 A | 7/1997 | Sun et al. |
| 5,728,748 A | 3/1998 | Sun et al. |
| 5,879,400 A | 3/1999 | Merrill et al. |
| 6,017,975 A | 1/2000 | Saum et al. |
| 6,165,220 A | 12/2000 | McKellop et al. |

FOREIGN PATENT DOCUMENTS

| | | |
|---|---|---|
| EP | 0722973 A1 | 7/1996 |
| EP | 0729981 A1 | 9/1996 |
| WO | WO 95/21212 | 8/1995 |
| WO | WO 96/25127 | 8/1996 |
| WO | WO 97/29787 | 8/1997 |
| WO | WO 97/29793 | 8/1997 |
| WO | WO 98/01085 | 1/1998 |
| WO | WO 98/14223 | 4/1998 |

OTHER PUBLICATIONS

Amstutz, H. C. et al., Clinical Orthopaedics and Related Research, 276, 7–18 (1992).
Baker et al., J. Biomed Mater Res, 46, 573–581 (1999).
Bergmann, G. et al., Journal of Biomechanics, 26, 969–990 (1993).
Bhambri, S. et al., Transactions of the 45th Orthopaedic Research Society, p. 838 (1999).
Bloebaum, R. et al., Clinical Orthopaedics and Related Research, 269, 120–127 (1991).
Buchannan et al., 1998 Materials Congress, p. 148 (1998).
Campbell, P. et al., Journal of Biomedical Materials Research, 29, 127–131 (1995).
Chiba, J. et al., Clinical Orthopaedics and Related Research, 300, 304–312 (1994).

(List continued on next page.)

*Primary Examiner*—David J. Isabella
(74) *Attorney, Agent, or Firm*—Fulbright & Jaworski L.L.P.

(57) ABSTRACT

The present invention relates to the prevention and decrease of osteolysis produced by wear of the ultrahigh molecular weight polyethylene (UHMWPE). Methods are disclosed for the isolation of wear particles, preparation of implants exhibiting decreased wear in comparison to conventional UHMWPE and preparation of implants that cause decreased biological response in comparison to conventional UHMWPE. The implants created by these methods are also included in the present invention.

16 Claims, 14 Drawing Sheets

OTHER PUBLICATIONS

Essential Medical Physiology (Johnson, Ed.), 46, 635–650 (1992).
Essner, 6th WBC, 854 (2000).
Goldring, S. et al., Journal of Bone and Joint Surgery, 65A, 575–584 (1983).
Gonzalez, O. et al., Journal of Biomedical Materials Research, 30(4), 463–473 (1996).
Goodman, S. et al., Journal of Bone and Joint Surgery, 80B, 531–539 (1998).
Green, T. et al., Biomaterials, 19(24), 2297–2302 (1998).
Green, T. et al., Journal of Biomedical Materials Research, 53(5), 490–497 (2000).
Hamilton, J. et al., Trans 42nd Orthopaedic Research Society, (Feb. 1996).
Hamilton, J. et al., Trans 43rd Orthopaedic Research Society, 782 (Feb. 1997).
Harris, W., Clinical Orthopaedic and Related Research, 311, 46–53 (1995).
ISO/CD 14242–1.2, "Implants for Surgery–Wear of Total Hip Prostheses–Part I: Loading and Displacement Parameters of Wear Testing Machines and Corresponding Environmental Conditions for Test," Draft Stnadard, Oct. (1997).
Jasty, M. et al., Clinical Orthopaedics and Related Research, 308, 111–126 (1994).
Jiranek, W. et al., Journal of Bone and Joint Surgery, 75A, 863–879 (1993).
Johnston, R. et al., Journal of Bone and Joint Surgery, 51A, 1083–1094 (1969).
Livingston et al., Trans. ORS, 22, 141–24 (1997).
Lyons, B. et al., Radiolytic Formation and Decay of trans–Vinylene Unsaturation in Polyethylene, in Irradiation of Polymeric Materials: Processes, Mechanisms, and Applications, E. Reichmanis, C.W. Frank, and J.H. O'Donnell, Editors, American Chemical Society; Washington, D.C., p. 62–73 (1993).
Matthews et al., Biomaterials, p. 2033 (2000).
McKellop, H. et al., Clinical Orthopaedics and Related Research, 311, 3–20 (1995).
McKellop, H. et al., Journal of Orthopaedic Research, 17(2), 157–67 (1999).
Muratoglu, 45th ORS Trans, 99 (1999).
Niedzwiecki, S. et al., Transactions of the 25th, Society for Biomaterials, p. 150 (1999).
Oka, M. et al., "Wear–resistant properties of newly improved UHMWPE," Trans. 5th World Biomaterials Congress, 520 (1996).
Oonishi, H. et al., Journal of Materials Science: Materials in Medicine, 8, 11–18 (1997).
Oonishi, H. et al., Journal of Maaterials Science: Materials in Medicine, 7, 753–63 (1996).
Oonishi, H. et al., Radiation Physics and Chemistry, 39(6), 495 (1992).
Painter, P. et al., The Theory of Vibrational Spectroscopy and Its Application to Polymeric Materials, John Wiley, New York, p. 252 (1982).
Polineni, V. et al., J. 44th Annual ORS, 49 (1998).
Rose, R. et al., Journal of Orthopaedic Research, 2:4, pp. 393–400 (1984).
Rubin, Pathology, Second Ed. (1994).
Sanford, ORS Trans, 119 (1995).
Schmalzried, T. et al., Journal of Bone and Joint Surgery, 74A, 849–863 (1992).
Schmalzried, T. et al., Journal of Bone and Joint Surgery, 74A, 1130–1139 (1992).
Scott, M. et al., Transactions of the Sixth World Biomaterials Congress, 177 (2000).
Shanbhag, A. et al., Journal of Biomedical Materials Research, 28, 81–90 (1994).
Shanbhag A, et al., Journal of Bone and Joint Surgery, 76B, 60–67 (1994).
Shanbhag, A. et al., Clinical Orthopaedics and Related Research, 342, 205–17 (1997).
Streicher, R., The International Journal for Radiation Reactions, Processess and Industrial Applications, 31:4–6, 693–698 (1988).
Wang, A., et al., Biomaterials 17 (1995) No. 9, 865–871.
Willert, H.G. et al., Clinical Orthopaedics and Related Research, 258, 95–107 (1990).
Yamamoto et al., Trans 6th World Biomaterials Congress, 485 (2000).

CROSS-LINKED ULTRA-HIGH MOLECULAR WEIGHT POLYETHYLENE FOR MEDICAL IMPLANT USE

This application claims priority to, and is a divisional application of, U.S. application No. 09/792,690, filed Feb. 23, 2001 now U.S Pat. No. 6,547,828.

BACKGROUND OF THE INVENTION

1. Field of the Invention

The invention generally relates to the field of orthopaedic implants. Specifically the prevention and decrease of osteolysis produced by wear of ultrahigh molecular weight polyethylene (UHMWPE) bearing components. Methods are disclosed for the isolation of wear particles, preparation of implants having decreased wear and preparation of implants causing decreased biological response. The implants created by these methods are also included in the present invention.

2. Related Art

Ultrahigh molecular weight polyethylene (UHMWPE) is commonly used as an articulating, load-bearing surface in total joint arthoplasty due to its unique array of properties. UHMWPE offers toughness, low friction coefficient, and biocompatibility. (Baker et al., 1999) Total joint prosthesis, composed of various combinations of metal, ceramic, and polymeric components, suffer from limited service lives and wear of UHMWPE is the limiting factor. It has become apparent that wear debris from UHMWPE components may be a primary contributor to osteolysis, loosening and eventual revision surgery. With steady increases in human life expectancy, there is a driving need to significantly increase the effective lifetime of a single implant. A desire to use prosthetic implants in younger patients is another strong incentive for improving the wear resistance of UHMWPE. The present invention discloses a process to improve long term wear characteristics of prosthetic implants made with UHMWPE.

When a human joint is destroyed or damaged by disease or injury, surgical replacement (arthoplasty) is normally required. A total joint replacement includes components that simulate a natural human joint, typically:

(a) a more-or-less spherical ceramic or metal ball, often made of cobalt chromium alloy;

(b) attachment of a "stem", which is generally implanted into the core of the adjacent long bone; and (c) a hemispherical socket which takes the place of the acetabular cup and retains the spherical ball. This hemispherical joint typically is a metal cup affixed into the joint socket by mechanical attachments and is lined with UHMWPE. In this way, the ball can rotate, pivot, and articulate within the socket, and the stem, via the ball, can pivot and articulate.

One of the difficulties in constructing any device for implantation into the human body is the need to avoid adverse host biological responses. The probability of adverse host reaction is reduced when certain synthetic materials are used. For example, synthetic UHMWPE implants have minimal immunogenicity and are not toxic. However, the wear and breakdown of the UHMWPE components are known in the art to cause host cellular responses, which ultimately lead to revision surgery.

Histologic studies have demonstrated that wear of UHM-WPE from orthopaedic inserts leads to several reactions. First, the tissue surrounding implants that were constructed with UHMWPE has been shown to contain extremely small particles of UHMWPE that range from sub-micron to a few microns in size. While large particles of UHMWPE appear to be tolerated by the body, as is the intact solid wall of the UHMWPE implant, the body apparently does not tolerate smaller particles of UHMWPE. In fact, the small particles of UHMWPE can cause histiocytic reactions by which the body attempts to eliminate the foreign material. Agents released during this process cause wear debris induced osteolysis. This in turn can lead to loss of fixation and loosening of the prosthesis.

Numerous techniques have been proposed to improve wear resistance of UHMWPE in orthopaedic implants. In these instances, however, many of the new versions of articulating polymers have generally failed to demonstrate significant reduction in wear and often prove to be inferior to conventional polyethylene. Recent attempts at improving wear properties of UHMWPE use special pressure/temperature processing techniques, surface treatments, formation of composites with high modulus fibers, and cross-linking via ionizing irradiation or chemical agents. Some of these attempts are summarized below.

Temperature/Pressure Treatments

Special thermal and pressure treatments have been used to increase physical performance and wear resistance of UHM-WPE (e.g., U.S. Pat. Nos. 5,037,928 and 5,037,938). For example, "Hipping" (Hot Isostatic Pressing), produces material alleged to comprise fewer fusion defects, increased crystallinity, density, stiffness, hardness, yield strength and resistance to creep, oxidation, and fatigue. Clinical studies, however, indicate that "Hipping" treated UHMWPE may possess inferior wear resistance in comparison to conventional UHMWPE. The inferior wear resistance being due to increased stiffness which leads to increased contact stresses during articulation (Livingston et al., Trans. ORS, 22, 141–24, 1997).

Post-consolidation temperature and pressure treatment, such as solid phase compression molding (Zachariades, U.S. Pat. No. 5,030,402), have also been attempted. Zachariades utilized solid state processing to further consolidate and orient UHMWPE chains. Resistance to wear in orthopaedic implants, however, was not improved.

Surface Treatments

Focusing upon the surface of UHMWPE components, attempts have been made to decrease wear by increasing smoothness and/or lubricity of the UHMWPE components surface. A group from Howmedica used a heat pressing technique to melt the articulating surface and remove machine marks from the surface of UHMWPE components such that the "wearing in" of rough machine marks could be avoided. This modification, however, resulted in delamination and high wear due to the fact that high articulation—induced stresses were located in regions where there was a sharp transition in crystalline morphology (Bloebaum et al., Clin. Orthop. 269, 120–127, 1991).

Andrade et al. (U.S. Pat. No. 4,508,606) suggested oxidizing the surface of a wet hydrophobic polymer surface to reduce sliding friction. The preferred means included applying a radio frequency glow discharge to the surface. With this technique, surface chemistries were altered by changing the time of gas plasma exposure and by altering the gas composition. The invention was proposed for the treatment of catheters to decrease surface friction properties while in a wet state. Similarly, Farrar (World Patent Application No. WO 95 212212) proposed using gas plasma treatments to cross-link the surface of UHMWPE and, thereby, increase its wear resistance. None of the plasma treatments, however, were practical because any perceived benefit would most likely wear away with articulation.

Composites

Because creep may be a contributor to UHMWPE wear, investigators have also included high modulus fibers in polyethylene matrices to reduce plastic deformation. (U.S. Pat. No. 4,055,862 discloses a "poly-to-carbon polyethylene composite" which failed significantly via delamination. Recently, Howmedica reported that a PET/carbon fiber composite exhibited 99% less hip simulated wear than conventional polyethylene over ten million cycles. (Polineni, V. K. et al., J. 44$^{th}$ Annual ORS, 49, 1998.)

Cross-Linking

Radiation Induced Cross-Linking

In the absence of oxygen, the predominant effect of ionizing radiation on UHMWPE is cross-linking (Rose et al., 1984, Streicher et al., 1988). Cross-linking of UHMWPE forms covalent bonds between polymer chains which inhibit cold flow (creep) of individual polymer chains. Free radicals formed during irradiation, however, can exist indefinitely if termination by cross-linking or other forms of recombination do not occur. Furthermore, reacted intermediates are continuously formed and decayed. Exposure of these free radical species at any time (e.g., during irradiation, shelf-aging, or in vivo aging) to molecular oxygen or any other reactive oxidizing agent can result in their oxidation. Extensive oxidation leads to a reduction in molecular weight, and subsequent changes in physical properties, including wear resistance.

To reduce oxidation after gamma sterilization, some orthopaedic manufacturers have implemented techniques to irradiate their materials under conditions that encourage cross-linking and reduce oxidation. These techniques include use of inert gas atmospheres during all stages of processing, use of vacuum packaging, and post sterilization thermal treatments. Specific examples of these techniques are given below.

Howmedica has developed various means for reducing UHMWPE oxidation associated with processing, i.e., the continual use of an inert gas during processing (see U.S. Pat. Nos. 5,728,748; 5,650,485; 5,543,471; 5,414,049; and 5,449,745). These patents also describe thermal annealing of the polymer to reduce or eliminate free radicals. The annealing temperature which is claimed (room temperature to 135° C.), however, avoids complete melting of UHMWPE.

Johnson & Johnson has disclosed in a European patent application (EP 0737481 A1) a vacuum packaging method with subsequent irradiation sterilization to promote cross-linking and reduce short- and long-term oxidative degradation. The packaging environment can contain an inert gas and/or hydrogen to "quench" free radicals. The cross-linking/sterilization method is claimed to enhance UHMWPE wear resistance (Hamilton, J. V. et al., Scientific Exhibit, 64$^{th}$ AAOS Meeting, February 1997; Hamilton, J. V. et al., Trans 43$^{rd}$ ORS, 782, 1997.).

Biomet's World patent application Ser. No. 97/29787 discloses the gamma irradiation of a prosthetic component in an oxygen resistant container partially filled with a gas capable of combining with free radicals (e.g., hydrogen).

Oonishi/Mizuho Medical Company-Japan and other investigators from Mizuho Medical Company began cross-linking PE (polyethylene) by gamma irradiation in 1971 for their SOM hip implants. Since then, they have studied the effect of a wide range of sterilization doses up to 1,000 MegaRad (MRad) on the mechanical, thermal, and wear properties of UHMWPE. They have also studied the effects of different interface materials on wear and found that alumina or zirconia heads on 200 MRad irradiated UHMWPE liners produced the lowest wear rates (Oonishi, H. et al., Radiat. Phys. Chem., 39(6), 495, 1992; Oonishi, H. et al., Mat. Sci: Materials in Medicine, 7, 753–63, 1966; Oonishi, H. et al., J. Mat. Sci: Materials in Medicine, 8, 11–18, 1997).

Massachusetts General Hospital/Massachusetts Institute of Technology (MGH/MIT) has used irradiation (especially e-beam) treatments to cross-link UHMWPE. These treatments reduced simulator wear rates of hip components by 80 to 95% in comparison to non-sterilized controls (see, e.g., World Patent Application 97/29793). This technology enables UHMWPE to be cross-linked to a high degree; however, the degree of cross-linking is dependent upon whether the irradiated UHMWPE is in a solid or molten state. Massachusetts General Hospital/Massachusetts Institute of Technology (MGH/MIT) has also disclosed the crosslinking of UHMWPE at greater than about 1 MRad, preferably greater than about 20 MRad to reduce the production of fine particles (U.S. Pat. No. 5,879,400). They disclosed a wear rate of 8 mg/million cycles for the unirradiated pin and 0.5 mg/million cycles for the irradiated (20 MRad) UHMWPE pin.

Orthopaedic Hospital/University of Southern California has disclosed patent applications which seek to increase the wear resistance of UHMWPE hip components using irradiation followed by thermal treatment, such as remelting or annealing (World Patent Application WO 98/01085). Irradiation of the UHMWPE was disclosed at 1–100 MRad, more preferably 5–25 MRad, and most preferably 5–10 MRad. Wear rates were disclosed for various doses of irradiation. Using this method, UHMWPE cross-linking was optimized such that the physical properties were above ASTM limits.

In U.S. Pat. No. 6,165,220, McKellop et al., has disclosed the crosslinking of UHMWPE at 1–25 MRad, more preferably 1–15 MRad, and most preferably 10 MRad. Oxidation profiles were given for UHMWPE crosslinked with 5, 10, or 15 MRad. They did not look at the size or number of wear particles.

BMG's European Application (EP 0729981 A1) discloses a unique processing method for decreasing friction and abrasive wear of UHMWPE used in artificial joints. The method involves irradiating UHMWPE at a low dose to introduce a small number of cross-linking points. Irradiation is followed by uniaxial compression of melted material to achieve molecular and crystallite orientation. BMG's material demonstrated a significant reduction in pin-on-disk wear, but the reduction was not as significant as with highly cross-linked versions of UHMWPE (Oka, M. et al., "Wear-resistant properties of newly improved UHMWPE," Trans. 5$^{th}$ World Biomaterials Congress, 520, 1996).

In U.S. Pat. No. 6,017,975, Saum et al., has disclosed the crosslinking of UHMWPE at 0.5–10 MRad, and more preferably 1.5–6 MRad to improve wear properties. They determined the wear rate for MRad up to 5 MRad but did not look at the size and number of wear particles.

Yamamoto et al. discloses an analysis of the wear mode and morphology of wear particles from crosslinked ultrahigh molecular weight polyethylene. The ultrahigh molecular weight polyethylene was crosslinked at 0–150 MRad gamma irradiation. Yamamoto et al. stated that the size of both cup surface fibrils and wear debris decrease in proportion to the dose of gamma irradiation. (Yamamoto et al., Trans. 6$^{th}$ World Biomaterials Congress, 485, 2000).

Importantly, for these methods, thermal annealing of the polymer during or after irradiation causes the free radicals (generated during irradiation) to recombine and/or form a more highly cross-linked material. Reducing or quenching free radicals is extremely important because a lack of free radicals can prevent significant UHMWPE aging.

B. Chemical Cross-Linking

Like irradiation cross-linking, chemical cross-linking of UHMWPE has been investigated as a method for increasing wear resistance. Chemical cross-linking provides the benefit of cross-linking while avoiding the degradative effects of ionizing irradiation.

The Orthopaedic Hospital/University of Southern California has submitted patent applications for cross-linking UHMWPE in order to increase wear resistance in orthopaedics (European Patent Application EP 0722973 A1), including a method wherein the cross-linking results in a material with a decreased crystallinity. Cross-linking is accomplished by irradiation in a molten state or photo cross-linking in a molten state, or cross-linking with a free radical generating chemical, and annealing the cross-linked polymer to pre-shrink it. Residuals from the chemical cross-linking reaction, however, are a regulatory concern and may contribute to long-term oxidative degradation.

It remains an object of the present invention, therefore, to provide a process for treating UHMWPE for use in orthopaedic implants such that the long-term wear properties of the UHMWPE are improved.

It is another object of the present invention to provide a process for treating UHMWPE for use in orthopaedic implants in vivo such that the performance of the implants in situ is improved.

It is well known in the published clinical literature that fine (micrometer and sub-micrometer sized) wear debris produced from bearing articulation of orthopaedic implants can elicit a macrophage cell-mediated response in the host body, which eventually leads to aseptic loosening of the implants and need for revision surgery. In general, bearing couples are formed from a combination of a soft material-ultra high molecular weight polyethylene (UHMWPE)-articulating against a hard material-metal or ceramic. It is the soft UHMWPE material which suffers the predominant wear in this soft-on-hard wear couple. Improvements in the wear resistance of UHMWPE, therefore, are expected to reduce the generation of fine particulate debris during articulation.

Although related art explicitly acknowledges the role particulate wear debris in the cell-mediated cascade which ultimately leads to aseptic loosening and revision surgery, it only anticipates a one-to-one relationship between improvements in gravimetric wear resistance and reduction in wear particulate debris numbers. The art explicitly or implicitly assumes a reduction in gravimetric wear will result in a concomitant reduction in the generation of wear particles. The teachings of the art do not necessarily result in the desired reductions in the generation of wear particles.

The prior art teaches that increased crosslinking energy corresponds to a decreased gravimetric wear. It presumes that this corresponds to a decrease in the number of wear particles. It also presumes that this corresponds to a decrease in the biological reaction to the wear debris produced, which may be false. The inventors of the present invention have found that decreased gravimetric wear does not necessarily correlate with decreased particle number and therefore may not correlate to decreased biological reaction. The present invention illustrates that there is not a continuum between crosslinking energy dose and the generation of wear particles.

The uniqueness of this work is that when crosslinking medical grade UHMWPE with gamma irradiation, the art is inadequate in predicting a relationship between the absorbed radiation dose and generation of wear debris in hip simulator testing. Within the range of acceptable dose, ranging from 5 MRad (significant reduction in gravimetric wear) to 15 MRad (acceptable upper limit for material strength considerations), the 10 MRad dose has been shown to fulfill the requirement for reduced wear debris generation. Alternative sources of irradiation (e.g., electron beam), or other gamma radiation doses between 5 and 15 MRad are predicted to also reduce the generation of particulate debris.

Recently, Green et al. (Green et al., 2000) found that smaller UHMWPE particles (0.24 $\mu$m) produced bone resorbing activity in vitro at a lower volumetric dose than larger particles (0.45 $\mu$m and 1.71 $\mu$m). This evidence suggests that finer wear particles may elicit a greater macrophage response than larger particles. Thus, finer wear debris generated at orthopaedic bearing couples should be fully characterized to accurately predict macrophage response. This is particularly important for new bearing materials, such as crosslinked UHMWPE, which have been reported by Bhambri et al. (Bhambri et al., 1999) to generate smaller wear particles (mean diameter of less than 0.1 $\mu$m) than conventional UHWMPE liners when tested in a hip simulator.

Because the cellular response to wear debris has been found to be dependent upon particle number and size, among other factors, the introduction of a new orthopaedic bearing material should be supported by an accurate description of wear particle parameters. The present invention teaches that filter membranes with very fine pore sizes (at most 0.05 $\mu$m) should be used to isolate UHMWPE wear debris from joint simulator serum and periprosthetic tissue to ensure an accurate description of particle characteristics.

Prior to the present invention, there was not an accurate way to predict the number and size of wear particles of UHMWPE. There was an assumption in the art the increasing radiation caused decreased wear resistance. The methods used in the art use filters with too large of a pore size and, consequently, many of the smaller particles pass through the filter and are not detected. A large number of the particles created by wear of UHMWPE were being missed by the previous detection method.

SUMMARY OF THE INVENTION

Therefore, it is an objective of the present invention to provide methods and medical implants related to the prevention and decrease of osteolysis produced by wear of the ultrahigh molecular weight polyethylene (UHMWPE).

An embodiment of the present invention is a method for isolating wear particles from an ultrahigh molecular weight polyethylene (UHMWPE) medical implant for use in the body comprising the steps of: crosslinking the UHMWPE; annealing the UHMWPE; machining UHMWPE to form an implant; wear testing the implant; harvesting wear particles; and filtering the particles using 0.05 $\mu$m or smaller pore size filters. The machining may be performed before crosslinking. The crosslinking may be performed using electromagnetic radiation or energetic subatomic particles. The crosslinking may be performed using gamma radiation, e-beam radiation, or x-ray radiation. In another aspect of the invention, the crosslinking may be performed using chemical crosslinking. The crosslinking may be at a dose of greater than five but less than or equal to fifteen MegaRad (MRad) or at a dose of greater than five but less than or equal to ten MegaRad (MRad). Annealing may be performed in the melt stage. In a further aspect of the invention, the annealing may be performed in an inert or ambient environment. The annealing may be performed below or equal to 150° C. The crosslinking may be sufficient to form an implant with a trans-vinylene index of greater than or equal to 0.10 or greater than about 0.15 and less than about 0.20. In another aspect of the present invention, the annealing is performed below about 150° C. and above about 140° C. and the crosslinking is sufficient to form an implant with a trans-vinylene index of greater than or equal to 0.10 or greater than about 0.15 and less than about 0.20. In another aspect, the annealing may be performed at 147° C. The crosslinking may be sufficient to form an implant with a trans-vinylene index of greater than or equal to 0.10 or greater than about 0.15 and less than about 0.20. In another aspect of the present invention, the annealing may be performed at 140° C. The crosslinking may be sufficient to form an implant with a trans-vinylene index of greater than or equal to 0.10 or greater than about 0.15 and less than about 0.20. Wear testing may occur on a joint simulator. The joint simulator may simulate the hip joint or knee joint of a human. The wear testing may occur in vivo. The harvesting may be performed using acid digestion, base digestion, or enzymatic digestion. The implant may have a polymeric structure with greater than about 300 angstrom lamellar thickness.

Another embodiment of the present invention is a method of preparing an UHMWPE medical implant for use in the body having a decreased wear particle number comprising the steps of: crosslinking the UHMWPE; annealing the UHMWPE; and machining UHMWPE to form an implant; wherein the wear particles that are decreased in number are greater than 0.125 $\mu$m in diameter. The machining may be performed before crosslinking. The crosslinking may be performed using electromagnetic radiation or energetic subatomic particles. The crosslinking may be performed using gamma radiation, e-beam radiation, or x-ray radiation. In another aspect of the invention, the crosslinking may be performed using chemical crosslinking. The crosslinking may be at a dose of greater than five but less than or equal to fifteen MegaRad (MRad) or at a dose of greater than five but less than or equal to ten MegaRad (MRad). Annealing may be performed in the melt stage. In a further aspect of the invention, the annealing may be performed in an inert or ambient environment. The annealing may be performed below or equal to 150° C. The crosslinking may be sufficient to form an implant with a trans-vinylene index of greater than or equal to 0.10 or greater than about 0.15 and less than about 0.20. In another aspect of the present invention, the annealing is performed below about 150° C. and above about 140° C. and the crosslinking is sufficient to form an implant with a trans-vinylene index of greater than or equal to 0.10 or greater than about 0.15 and less than about 0.20. In another aspect, the annealing may be performed at 147° C. The crosslinking may be sufficient to form an implant with a trans-vinylene index of greater than or equal to 0.10 or greater than about 0.15 and less than about 0.20. In another aspect of the present invention, the annealing may be performed at 140° C. The crosslinking may be sufficient to form an implant with a trans-vinylene index of greater than or equal to 0.10 or greater than about 0.15 and less than about 0.20. Wear testing may occur on a joint simulator. The joint simulator may simulate the hip joint or knee joint of a human. The wear testing may occur in vivo. The harvesting may be performed using acid digestion, base digestion, or enzymatic digestion. The implant may have a polymeric structure with greater than about 300 angstrom lamellar thickness.

Yet another embodiment of the present invention is a method of decreasing macrophage response to an UHMWPE medical implant for use in the body comprising the steps of: performing wear particle analysis; and crosslinking the UHMWPE at a dose level exhibiting the lowest particle number per million cycles of the hip simulator wherein the number of particles present was determined using a 0.05 $\mu$m or smaller pore size filter.

Still another embodiment of the present invention is a method of decreasing macrophage response to an UHMWPE medical implant in the body comprising crosslinking UHMWPE prior to implantation in a patient wherein the total volume of wear particles is decreased and the total number of wear particles is decreased. The crosslinking may be performed using electromagnetic radiation or energetic subatomic particles. In an aspect of the present invention, crosslinking may be performed using gamma radiation, e-beam radiation, or x-ray radiation or chemical crosslinking. In another aspect of the invention, the crosslinking may be at a dose of greater than five but less than or equal to fifteen MegaRad (MRad) or greater than five but less than or equal to ten MegaRad (MRad).

Another embodiment of the present invention is a method of decreasing macrophage response to an UHMWPE medical implant for use in the body comprising the steps of: crosslinking the UHMWPE; annealing the UHMWPE; machining UHMWPE to form an implant; wear testing the implant; harvesting wear particles; filtering the particles using 0.05 $\mu$m or smaller pore size filters; characterizing the wear particles; determining the number of particulate debris; and selecting the crosslinking method for implants that gives the lowest number of particulate debris. The machining may be performed before crosslinking. The crosslinking may be performed using electromagnetic radiation or energetic subatomic particles. The crosslinking may be performed using gamma radiation, e-beam radiation, or x-ray radiation. In another aspect of the invention, the crosslinking may be performed using chemical crosslinking. The crosslinking may be at a dose of greater than five but less than or equal to fifteen MegaRad (MRad) or at a dose of greater than five but less than or equal to ten MegaRad (MRad). Annealing may be performed in the melt stage. In a further aspect of the invention, the annealing may be performed in an inert or ambient environment. The annealing may be performed below or equal to 150° C. The crosslinking may be sufficient to form an implant with a trans-vinylene index of greater than or equal to 0.10 or greater than about 0.15 and less than about 0.20. In another aspect of the present invention, the annealing is performed below about 150° C. and above about 140° C. and the crosslinking is sufficient to form an implant with a trans-vinylene index of greater than or equal to 0.10 or greater than about 0.15 and less than about 0.20. In another aspect, the annealing may be performed at 147° C. The crosslinking may be sufficient to form an implant with a trans-vinylene index of greater than or equal to 0.10 or greater than about 0.15 and less than about 0.20. In another aspect of the present invention, the annealing may be performed at 140° C. The crosslinking may be sufficient to form an implant with a trans-vinylene index of greater than or equal to 0.10 or greater than about 0.15 and less than about 0.20. Wear testing may occur on a joint simulator. The joint simulator may simulate the hip joint or knee joint of a human. The wear testing may occur in vivo. The harvesting may be performed using acid digestion, base digestion, or enzymatic digestion. The implant may have a polymeric structure with greater than about 300 angstrom lamellar thickness. In another embodiment of the invention, the characterization may be by a high resolution microscopic method or an automatic particle counter. In a further aspect of the present invention, the characterization may be by scanning electron microscopy or automatic particle counter.

Yet another embodiment of the present invention is a method of decreasing macrophage response to an UHMWPE medical implant for use in the body comprising the steps of: crosslinking the UHMWPE; annealing the UHMWPE; machining UHMWPE to form an implant; wear testing the implant; harvesting wear particles; filtering the particles using 0.05 µm or smaller pore size filters; characterizing the wear particles; determining the number of particulate debris; determining the total particle surface area; and selecting the crosslinking method for implants that gives the lowest total particle surface area. Machining may be performed before said crosslinking.

Still another embodiment of the present invention is a method of decreasing osteolysis of an UHMWPE medical implant for use in the body comprising the steps of: crosslinking the UHMWPE; annealing the UHMWPE; machining UHMWPE to form an implant; wear testing the implant; harvesting wear particles; filtering the particles over 0.05 µm or smaller pore size filters; characterizing the wear particles; determining the number of particulate debris; and selecting the crosslinking dose level to crosslink implants that exhibits the lowest number of particulate debris. The machining may be performed before crosslinking. The crosslinking may be performed using electromagnetic radiation or energetic subatomic particles. The crosslinking may be performed using gamma radiation, e-beam radiation, or x-ray radiation. In another aspect of the invention, the crosslinking may be performed using chemical crosslinking. The crosslinking may be at a dose of greater than five but less than or equal to fifteen MegaRad (MRad) or at a dose of greater than five but less than or equal to ten MegaRad (MRad). Annealing may be performed in the melt stage. In a further aspect of the invention, the annealing may be performed in an inert or ambient environment. The annealing may be performed below or equal to 150° C. The crosslinking may be sufficient to form an implant with a trans-vinylene index of greater than or equal to 0.10 or greater than about 0.15 and less than about 0.20. In another aspect of the present invention, the annealing is performed below about 150° C. and above about 140° C. and the crosslinking is sufficient to form an implant with a trans-vinylene index of greater than or equal to 0.10 or greater than about 0.15 and less than about 0.20. In another aspect, the annealing may be performed at 147° C. The crosslinking may be sufficient to form an implant with a trans-vinylene index of greater than or equal to 0.10 or greater than about 0.15 and less than about 0.20. In another aspect of the present invention, the annealing may be performed at 140° C. The crosslinking may be sufficient to form an implant with a trans-vinylene index of greater than or equal to 0.10 or greater than about 0.15 and less than about 0.20. Wear testing may occur on a joint simulator. The joint simulator may simulate the hip joint or knee joint of a human. The wear testing may occur in vivo. The harvesting may be performed using acid digestion, base digestion, or enzymatic digestion. The implant may have a polymeric structure with greater than about 300 angstrom lamellar thickness. In another embodiment of the invention, the characterization may be by a high resolution microscopic method or an automatic particle counter. In a further aspect of the present invention, the characterization may be by scanning electron microscopy or automatic particle counter.

Another embodiment of the present invention is a method of decreasing osteolysis of an UHMWPE medical implant for use in the body comprising the steps of: crosslinking the UHMWPE; annealing the UHMWPE; machining UHMWPE to form an implant; wear testing the implant; harvesting wear particles; filtering the particles using 0.05 µm or smaller pore size filters; characterizing the wear particles; determining the number of particulate debris; determining the total particle surface area; and selecting the crosslinking method for implants that gives the lowest total particle surface area. Machining is performed before said crosslinking.

Yet another embodiment of the present invention is a method of decreasing macrophage response to a UHMWPE medical implant for use in the body comprising the steps of crosslinking the UHMWPE, simulating use in a host, and testing serum for particulate debris using a 0.05 µm pore size filter, wherein particles of the diameter of 0.1 µm to 1 µm cause increased macrophage response. The machining may be performed before crosslinking. The crosslinking may be performed using electromagnetic radiation or energetic subatomic particles. The crosslinking may be performed using gamma radiation, e-beam radiation, or x-ray radiation. In another aspect of the invention, the crosslinking may be performed using chemical crosslinking. The crosslinking may be at a dose of greater than five but less than or equal to fifteen MegaRad (MRad) or at a dose of greater than five but less than or equal to ten MegaRad (MRad). Wear testing may occur on a joint simulator. The joint simulator may simulate the hip joint or knee joint of a human.

Still another embodiment of the present invention is a cross-linked UHMWPE medical implant for use in the body that exhibits decreased osteolysis (or macrophage response) in comparision to conventional treatment of UHMWPE due to a particle number of less than $5 \times 10^{12}$ per year upon testing for wear resistance.

Another embodiment of the present invention is an UHMWPE medical implant for use in the body having a decreased wear particle number of particles created by the steps comprising of: crosslinking the UHMWPE; annealing the UHMWPE; machining UHMWPE to form an implant; wear testing the implant; harvesting wear particles; filtering the particles over 0.05 µm or smaller pore size filters; characterizing the wear particles; determining the number of particulate debris; and selecting the crosslinking method to crosslink implants that exhibits the lowest number of particulate debris; wherein the wear particles that are decreased in number are greater than 0.125 µm in diameter. The machining may be performed before crosslinking. The crosslinking may be performed using electromagnetic radiation or energetic subatomic particles. The crosslinking may be performed using gamma radiation, e-beam radiation, or x-ray radiation. In another aspect of the invention, the crosslinking may be performed using chemical crosslinking. The crosslinking may be at a dose of greater than five but less than or equal to fifteen MegaRad (MRad) or at a dose of greater than five but less than or equal to ten MegaRad (MRad). Annealing may be performed in the melt stage. In a further aspect of the invention, the annealing may be performed in an inert or ambient environment. The annealing may be performed below or equal to 150° C. The crosslinking may be sufficient to form an implant with a trans-vinylene index of greater than or equal to 0.10 or greater than about 0.15 and less than about 0.20. In another aspect of the present invention, the annealing is performed below about 150° C. and above about 140° C. and the crosslinking is sufficient to form an implant with a trans-vinylene index of greater than or equal to 0.10 or greater than about 0.15 and less than about 0.20. In another aspect, the annealing may be performed at 147° C. The crosslinking may be sufficient to form an implant with a trans-vinylene index of greater than or equal to 0.10 or greater than about 0.15 and less than about 0.20. In another aspect of the present invention, the annealing may be performed at 140° C. The crosslinking may be sufficient to form an implant with a trans-vinylene index of greater than or equal to 0.10 or greater than about 0.15 and less than about 0.20. Wear testing may occur on a joint simulator. The joint simulator may simulate the hip joint or knee joint of a human. The wear testing may occur in vivo. The harvesting may be performed using acid digestion, base digestion, or enzymatic digestion. The implant may have a polymeric structure with greater than about 300 angstrom lamellar thickness. In another aspect of the invention, the characterization may be by a high resolution microscopic method or an automatic particle counter. In a further aspect of the present invention, the characterization may be by scanning electron microscopy or automatic particle counter.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Definitions

Figure 1:
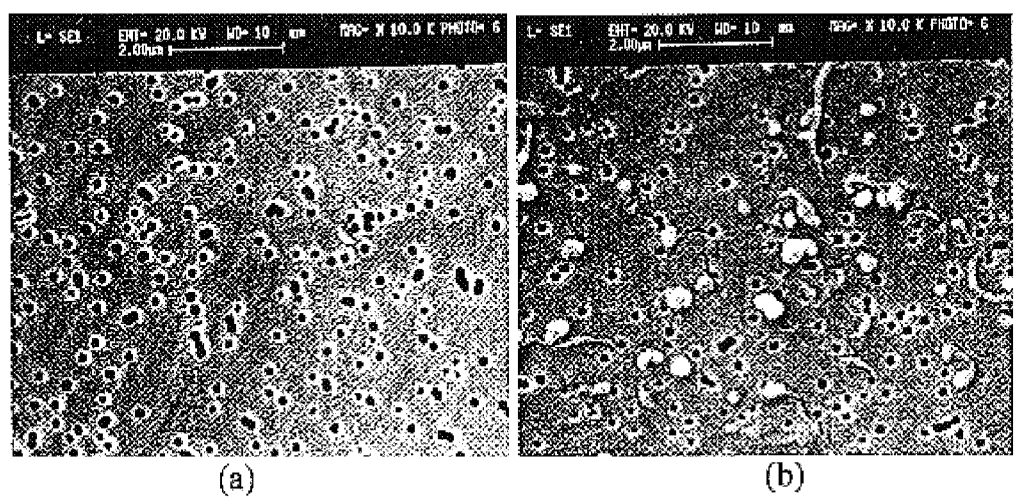
FIG. 1. SEM micrographs at 10,000× of (a) digested and filtered deionized water and (b) digested and filtered knee simulator serum.

Annealing, as used herein, refers to heating a sample, such as UHMWPE, and then allowing the sample to cool. Thermal annealing of the sample during or after irradiation causes the free radicals (generated during irradiation) to recombine and/or form a more highly cross-linked material.

Characterizing the wear particles, as used herein, refers to determining the size, shape, number, and concentration of the wear particles. It may include the use of, but is not limited to, using a microscopic method such as scanning electron microscopy, or an automatic particle counter.

Decreased or increased, as used herein, refers to a decrease or increase in a parameter in comparison to that parameter in conventional (not crosslinked) polyethylene.

Dose, as used herein, refers to the amount of radiation absorbed by the sample, such as UHMWPE.

Gravimetric, as used herein, refers to the measuring of weight loss.

In vivo, as used herein, refers to an activity occurring within the body of a subject, preferably a human subject.

Lamellar thickness, as used herein, is the depth of the layers of alternate amorphous and crystalline regions. The lamellar thickness (1) is the calculated thickness of assumed lamellar structures in the polymer using the following expression:

$$l=(2 \cdot \sigma_e \cdot T_m^\circ)/(\Delta H \cdot (T_m^\circ - T_m) \cdot \rho)$$

where $\sigma_e$ is the end free surface energy of polyethylene ($2.22 \times 10^{-6}$ cal/cm$^2$), $\Delta H$ is the heat of melting of polyethylene crystals (69.2 cal/g), $\rho$ is the density of the crystalline regions (1.005 g/cm$^3$), and $T_m^\circ$ is the melting point of a perfect polyethylene crystal (418.15 K).

Macrophage response, as used herein, refers to an adverse reaction that may lead to osteolysis of an implant.

MegaRad (MRad), as used herein, refers to a unit of measure for the energy absorbed per unit mass of material processed by irradiation (absorbed dose). The radiation dose may be within an error of ±10%. A MegaRad is equivalent to 10 kiloGray (kGy).

Osteolysis, as used herein, refers to the reabsorption of bone.

Trans-vinylene index (TVI), as used herein, is a based upon the concentration of trans-vinylene units (TVU) which have been shown to be linear with absorbed radiation dose for polyethylene at low dose levels. The concentration of TVU and thus the TVI, can be used to determine the level of crosslinking in UHMWPE. It can be used to determine the absolute dose level received during the crosslinking of UHMVPE. The TVI is calculated by normalizing the area under the trans-vinylene vibration at 965 cm$^{-1}$ to that under the 1900 cm$^{-1}$ vibration.

Ultra high molecular weight polyethylene, as used herein, refers to polyethylene having a molecular weight greater than 1.75 million.

Wear debris, as used herein, refers to particles generated from the articulation of the joint components.

Wear resistance, as used herein, refers to the property of resisting physical changes in the material due to articulation.

Wear testing, as used herein, articulating joint components. Wear testing includes testing in water, synovial fluid, or any lubricant.

Crosslinked ultrahigh molecular weight polyethylene (UHMWPE) and implants are useful as prostheses for various parts of the body, such as components of a joint in the body. For example, in the hip joints, they can be a prosthetic acetabular cup (as exemplified above), or the insert or liner of the cup, or a component of a trunnion bearing (e.g. between the modular head and the stem). In the knee joint, they can be a prosthetic tibial plateau (femoro-tibial articulation), patellar button (patello-femoral articulation), and trunnion or other bearing components, depending on the design of the artificial knee joint. For example, in knees of the meniscal bearing type, both the upper and lower surfaces of the UHMWPE component may be surface-crosslinked, i.e., those surfaces that articulate against metallic or ceramic surfaces. In the ankle joint, they can be the prosthetic talar surface (tibio-talar articulation) and other bearing components. In the elbow joint, they can be the prosthetic radio-humeral joint, ulno-humeral joint, and other bearing components. In the shoulder joint, they can be used in the glenoro-humeral articulation, and other bearing components. In the spine, they can be used in intervertebral disk replacement and facet joint replacement. They can also be made into temporo-mandibular joint (jaw) and finger joints. The above are by way of example, and are not meant to be limiting. This application often uses UHMWPE and acetabular cup implants as examples of UHMWPE and implants, respectively. However, it is to be understood that the present invention would be applicable to PE in general; and to implants in general.

Osteolysis is a common long-term complication in total hip replacement (THR) (Harris, 1995) and has been linked to wear debris generated from ultra high molecular weight polyethylene (UHMWPE) acetabular liners (Amstutz et al., 1992; Schmalzried et al., 1992; Willert et al., 1990; and Goldring et al., 1983). While the response of periprosthetic tissue to wear debris is not fully understood, macrophage response to particulate wear debris is believed to be an important factor in osteolysis (Goodman et al., 1998; Jasty et al., 1994; Chiba et al., 1994; and Jiranek et al., 1993). It is well established that the cellular response to wear debris is dependent upon particle number, shape, size, surface area, and material chemistry, among other factors (Green et al., 1998; Gonzalez et al., 1996; and Shanbhag et al., 1994). The introduction of new bearing materials, such as crosslinked UHMWPE, should therefore be supported by accurate descriptions of the number, size distribution, surface area, and volume of wear particles generated.

Various techniques have been developed to isolate UHMWPE wear particles from periprosthetic tissue and joint simulator serum. Common protocols involve digestion of tissue or serum samples in either a strong base or acid, followed by filtration of the digests through filter membranes with a pore size of 0.2 $\mu$m (McKellop et al., 1995; Campbell et al., 1995; and Niedzwiecki et al., 1999). A scanning electron microscope (SEM) is used to determine the numbers, sizes, and shapes of particles deposited on the filter membrane. Previous analyses of particles recovered from the periprosthetic tissues of THR patients and from hip simulator serum indicated that the mode of the particle size distribution was at or below the pore size (0.2 $\mu$m) of the filter membrane (McKellop et al., 1995). Thus, a significant number of particles having a diameter below 0.2 $\mu$m may have passed through the filter pores and not been detected during the analyses. It is therefore hypothesized that the number of UHMWPE particles generated by THR bearing components are underestimated by particle isolation techniques which involve filtration of debris through a 0.2 $\mu$m filter membrane.

In the present invention, hip simulator testing was conducted on three classes of materials (1) conventional (non-irradiated) UHMWPE (C-PE), (2) 5 MRad gamma irradiation crosslinked UHMWPE (5-XLPE), and (3) 10 MRad gamma irradiation crosslinked UHMWPE (10-XLPE). According to published literature, 5-XLPE and 10-XLPE are both expected to exhibit enhanced wear resistance compared to C-PE, with the degree of improvement increasing with increasing radiation dose. Gravimetric analyses showed the expected trends to hold up to a duration of 15 million cycles tested to-date. However, when analyzed for particulate debris, it was discovered that the 5-XLPE material began to generate more wear debris than C-PE approximately at approximately 5 million cycle. The 10-XLPE material, on the other hand, showed fewer particles for the entire duration of testing. Crosslinking affects the size of particles. It is ideal to decrease the total volume of particles and the number of particles at all sizes.

Crosslinking of UHMWPE

The wear process in an artificial joint is a multi-directional process. Crosslinking is achieved by using high doses of radiation. In the absence of oxygen, crosslinking is the predominant effect of ionizing radiation on UHMWPE (Rose et al., 1984, Streicher et al., 1988). Crosslinking of UHMWPE forms covalent bonds between polymer chains which inhibit cold flow (creep) of individual polymer chains. Crosslinking UHMWPE provides a lower wear rate because the polymer chains form a network that is more stable to multi-directional movements. When irradiated at temperatures above 150° C., a permanent intermolecular homogeneous network is formed. Exposure of UHMWPE to irradiation results in the cleavage of carbon-carbon and carbon-hydrogen bonds within the polyethylene chains. Such irradiation includes but is not limited to energetic subatomic particles, gamma, electron beam, or x-ray radiation. Gamma irradiation is known to break polymer chains and create free radicals, that react with oxygen in the atmosphere or synovial fluid. This oxidation reaction causes further chain scission and leads to the formation of an embrittled region close to the polymer surface (Buchanan et al., 1998, Materials Congress 1998, p.148). Oxidation of free radicals formed during irradiation leads to a reduction in molecular weight, and subsequent changes in physical properties, including wear resistance. Formation of free radicals during irradiation primarily include a combination of alkyl and allyl type free radicals. In the presence of oxygen, however, a small fraction of peroxy radicals are also formed. To reduce the formation of peroxy radicals, the process is performed under vacuum or in the presence of an inert gas, such as argon. Free radicals can be removed through either addition of antioxidants or through remelting. Remelting is a process in which the implants are reheated to increase chain mobility, so the free radicals can recombine or terminate. The overall industrial process is to radiate polymer sheets, which are remelted. From the remelted sheets implants are machined and thereafter sterilized.

It is well known in the art that crosslinking of UHMWPE by a number of means, including irradiation with energetic beams (gamma rays, electron beams, x-rays, etc.,) or by chemical means improves the wear resistance of the material. Although clinical use of crosslinked UHMWPE was first reported in the 1970's it was not until the mid 1990's that anatomic joint (hip and knee) simulator tests were conducted to demonstrate the enhanced wear resistance of crosslinked UHMWPE. The extant literature and art teaches methods by which UHMWPE can be crosslinked to varying degrees and demonstrates improvements in wear resistance in joint simulator testing.

The present invention includes all forms of crosslinking, crosslinking at all temperatures, crosslinking in the presence or absence of an inert environment, and in the presence or absence of free-radical scavengers. Crosslinking may occur before or after the implant is formed (machined).

Macrophage Response and Osteolysis

The major cause of late-term implant failure is implant induced osteolysis and aseptic loosening of hip replacements. Osteolysis is the reabsorption of bone, in this case due to a reaction to polyethylene wear debris. The majority of wear particles produced by implants are thought to be submicron in size. Patient tissue examined in revision operations show a periprosthetic pseudo-membrane containing macrophages and multinucleated giant cells (osteoclasts, which can be viewed as specialized macrophages) associated with polyethylene particles. The wear debris stimulates macrophages to produce mediators of osteolysis which causes aseptic loosening of the implant. Mediators produced by the macrophages include IL-1$\beta$, IL-6, TNF$\alpha$, GM-CSF, PGE$_2$, and enzymes such as collagenase. IL-6 stimulates the formation of osteoclasts and thus stimulates bone resorption. IL-1$\beta$ stimulates proliferation and maturation of progenitor cells into osteoclasts. IL-1$\beta$ also stimulates osteoblasts causing maturation of the osteoclast into multinucleate bone reabsorbing cells. TNF$\alpha$ has much the same function as IL1$\beta$ in this situation (Green et al., 1998). The ruffled border of osteoclasts releases acids and hydrolytic enzymes that dissolve proteins and minerals. Osteoblasts create bone by synthesizing proteins. Osteoblasts secrete collagenase, which may facilitate osteoclast activation. Osteoblasts produce TGF$\beta$, IGF1, IGF2, PDGF, IL1, FGF, TNF$\alpha$ that regulate growth and differentiation of bone (Pathology, Rubin, Second Ed. 1994; Essential Medical Physiology, Johnson, 1992). The biological activity of polyethylene wear debris is dependent upon the size and number of particles present (Matthews et al., 2000 Biomaterials, p. 2033). Matthews et al. found particles of the size 0.24, 0.45, and 1.7 $\mu$m to be the most biologically active. This finding was based on cell studies in which the wear debris was filtered over 10, 1.0, 0.4, and 0.1 $\mu$m pore size filters. Wear particles were co-cultured with donor macrophages and the production of mediators was measured. The specific biological activity (SBA) of the wear debris is calculated using the equation:

$$SBA = [B(r) \times C(c)]_{0.1-1.0\ \mu m} + [B(r) \times C(c)]_{1-10\ \mu m} + [B(r) \times C(c)]_{10-100\ \mu m}$$

Where B(r) is the biological activity function of a given particle size and C(c) is the volumetric concentration of the wear debris for a given particle size. The functional biological activity (FBA) is the product of the wear volume and the SBA (Fisher et al., 2000 46$^{th}$ ORS Meeting).

Methods of Wear Analysis

Joint simulator wear testing of orthopaedic bearing components reproduces in vivo wear mechanisms. A common means of verifying the reproduction of clinical wear mechanisms is to compare the wear debris of laboratory and retrieved specimens (McKellop et al., 1995). UHMWPE debris can be isolated from both retrieved periprosthetic tissue and simulator-tested serum using a method developed by Campbell et al. (Campbell et al., 1995). This widely accepted method uses base digestion of the serum, centrifugation, and density gradients to isolate UHMWPE debris. However, the process is labor intensive and expensive. An alternative method for isolating UHMWPE wear debris from simulator-tested serum includes an acid treatment and vacuum filtration to isolate particles (Scott et al., 2000). Collected wear debris can then be mounted, sputter coated with gold, and analyzed by scanning electron microscopy (SEM). SEM can be used to determine the numbers, size, and shapes of particles. FTIR spectra of the debris can be compared with those of a control substance, such as HDPE, to determine the identity of the wear debris.

Gravimetric Measurement

Wear resistance can also be defined and determined by gravimetric means, by measuring the weight loss of the UHMWPE component at fixed intervals of the test duration. Gravimetric measurement provides the change in weight from before testing to after testing. The gravimetric wear rate is defined in milligrams/million cycles of the simulator. It provides a measurement of the total mass of debris generated from wear surfaces. It does not give any information regarding the size and number of wear particles. This method is not accurate when the material absorbs fluid. UHMWPE does absorb fluid. It was previously believed that gravimetrically measured reduction in wear translated into reduction in particle generation. Thus, it was assumed that a decrease in weight loss correlated with decreased wear and decreased particle characteristics. Therefore, it would be expected that there would be a decrease in osteolysis as well. There is no predictable relationship between total wear mass and particulate number. This is explained by the following equation:

$$V_{total\ wear} = \sum_{i=1}^{N} V_{each\ particle}$$

where N is the number of particles. For instance, if crosslinking reduces the average volume of individual particles, then a greater number of particles will be produced per unit volume of total wear. On the other hand, if crosslinking increases the average particle volume, then there are fewer particles per unit volume of total wear. Thus, particle size dictates the number of particles produced per unit volume of total wear. Gravimetric methods cannot measure individual particle parameters such as size, volume and number. Thus, gravimetric techniques are limited and do not provide a means to measure and evaluate these individual particle characteristics.

Joint Simulators

Joint simulators include hip simulators, knee simulators and other joint simulators. In one use of a hip simulator, UHMWPE acetabular liners are articulated against CoCrMo heads. Commercially available acetabular liners are machined from ram-extruded UHMWPE and sterilized using ethylene oxide. The liners were inserted into Ti-6A1-4V acetabular shells and tested against 32 mm diameter CoCr femoral heads. The bearing couples are tested under physiological loading and motion conditions (Bergmann et al., 1993; Johnston and Schmidt, 1969; and ISO/CD 14242-1.2) on a 12-station hip simulator. Test duration can range from 1 million to 30 million cycles (Mcycles) at a cyclic frequency of 1 Hz, representing 1 to 30 years of normal service in the human host. The test lubricant is bovine serum containing 0.2% sodium azide and 20 mM EDTA. The test serum is replaced approximately every 500,000 cycles.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1
Validation of an Acid Digestion Method for Isolating UHMWPE Wear Debris from Joint Simulator Serum The particle isolation method was performed on the following samples: (1) deionized water; (2) untested bovine calf serum; (3) deionized water pumped through silicone tubing at 37° C. for one week; and (4) simulator-tested serum from four separate stations on an AMTI knee simulator. The sera from the knee simulator were harvested at about 500,000 cycles and contained between 1 and 20 mg of UHMWPE debris (as determined by weight loss of UHMWPE tibial inserts). Ten ml of each sample was added to 40 ml of 37% HCl. A magnetic stir bar was added to the solution and stirred at 350 rpm at 50° C. for approximately one hour. At this time, 1 ml of the solution was removed and added to 100 ml of methanol. This solution was then filtered through a 0.2 $\mu$m pore size polycarbonate filter membrane. The filter membranes were mounted on metal microscope stubs, sputter coated with gold, and imaged using a scanning electron microscope (SEM). Image analysis was performed at 10,000× in order to determine contamination levels ("blank" samples 1 though 3) and to correlate observed wear with particle count density (simulator-tested sera). For each of the simulator-tested samples, a minimum of 500 particles and 20 fields of view were analyzed, and the particle count density was expressed in average number of particles per field. Additionally, the average particle volume per field (VFIELD) was calculated by dividing the total volume of analyzed particles in a sample by the number of fields needed to image all the particles. The volume of each particle was estimated using the following equation:

$$V_{PARTICLE} = \tfrac{4}{3}\pi(ECR)^3,$$

where ECR is the radius of a circle having the same area as the measured feature.

A representative SEM image of the filter membrane through which the digested deionized water sample was passed is shown in FIG. 1a. At 10,000×, no particles were seen on the filter membrane, indicating an absence of contaminants within the reagents used in the procedure. The filter membrane through which the digested untested serum was passed had a similar appearance, indicating that the proteins in the serum were completely digested by the HCl. Filtration of the water sample that was pumped through silicone tubing also resulted in an absence of particles. This suggests that the tubing though which serum is circulated in joint simulators releases insignificant levels of silicone debris. The digested sera from the knee simulator showed particulate material that was comprised of two predominant morphologies, spheroids and fibrils (FIG. 1b).

Figure 2:
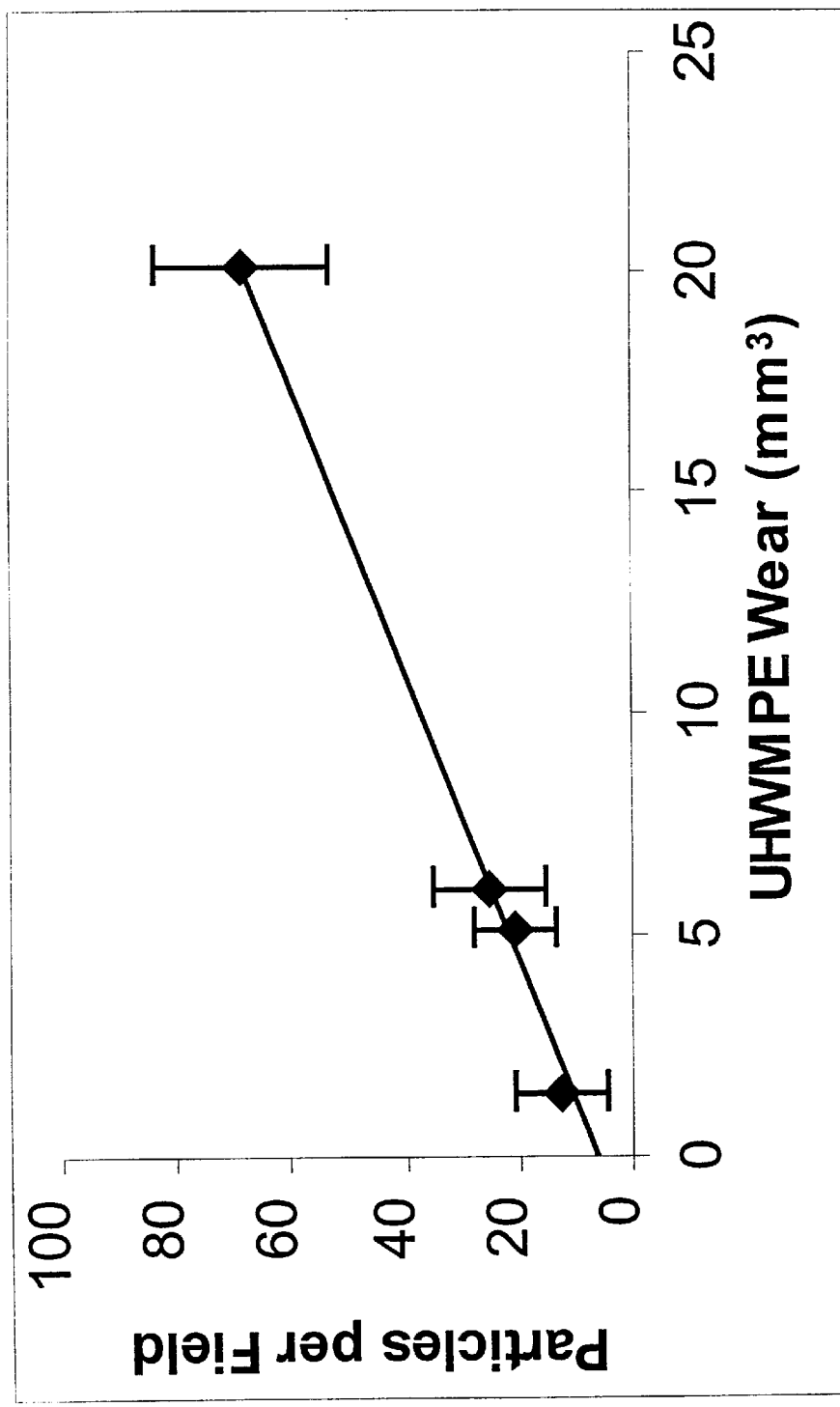
FIG. 2. Number of particles per field vs. measured UHMWPE wear for simulator-tested tibial inserts.
Figure 3:
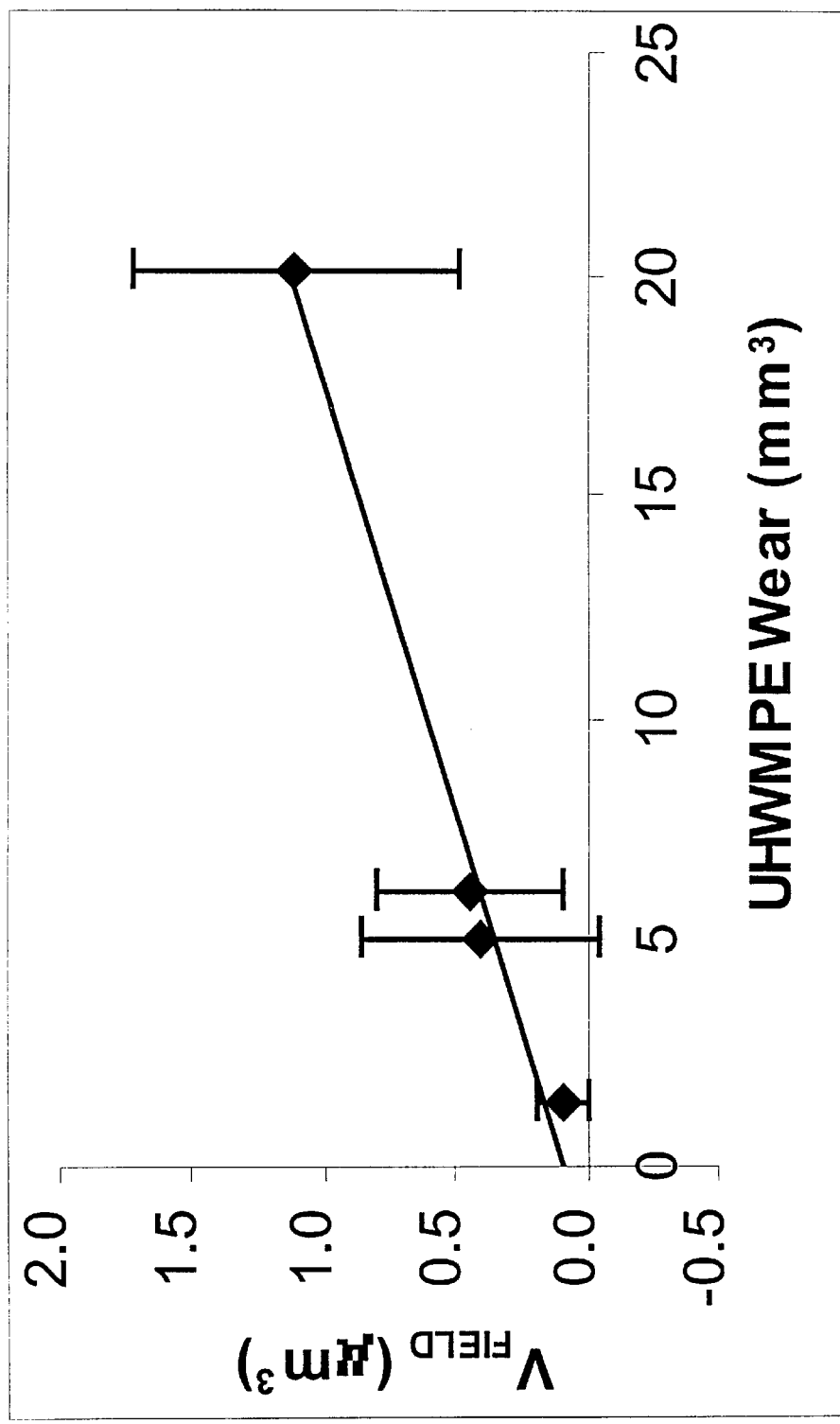
FIG. 3. Average particle volume per field (VFIELD) VS. UHMWPE wear for simulator-tested tibial inserts.

Quantitative image analysis revealed that the number of particles per field correlated strongly ($R^2$=0.997) with measured UHMWPE wear for the simulator-tested serum samples (FIG. 2). The average particle volume per field of view also correlated strongly ($R^2$=0.983) with measured UHMWPE wear (FIG. 3).

Example 2
Hip Simulator Specimens and Parameters

Commercially available acetabular liners were machined from ram-extruded GUR 1050 UHMWPE (Poly-Hi Solidur, Ft. Wayne, Ind.) and sterilized using ethylene oxide. The liners were inserted into Ti-6Al-4V (ISO 5832) acetabular shells and tested against 32 mm diameter CoCr femoral heads (ASTM F799). The bearing couples (n=3) were tested under physiological loading and motion conditions (Bergmann et al., 1993; Johnston and Schmidt, 1969; and ISO/CD 14242-1.2) on a 12-station AMTI (Watertown, Mass.) hip simulator. Testing was conducted to 12 million cycles (Mcycles) at a cyclic frequency of 1 Hz. The test lubricant was bovine serum (Hyclone Laboratories, Logan, Utah) which contained 0.2% sodium azide and 20 mM EDTA. The test serum was replaced approximately every 500,000 cycles.

Example 3
Isolation of UHMWPE Particles

Eight serum samples were harvested during the 12 million cycle test. The test interval (in cycles) for each serum sample is listed in Table 1. Each sample was collected in an Erlenmeyer flask containing a stirbar and stirred overnight at 350 rpm. Ten ml of serum was then added to 40 ml of 37% w/V HCl and stirred for one hour at 50° C. One ml of the digested solution was added to 100 ml of methanol, which was then filtered through a 0.2 $\mu$m pore size polycarbonate filter membrane. A replicate digest was filtered through a 0.05 $\mu$m pore size membrane for each serum sample.

TABLE 1

Data on Serum Samples Harvested from a Hip Simulator.

| Serum Sample | Testing Interval ($10^6$ cycles) | $N_F$* (0.2 $\mu$m pore size filters) | $N_F$* (0.05 $\mu$m pore size filters) | $N_C$§ ($10^6$) (0.2 $\mu$m pore size filters) | $N_C$§ ($10^6$) (0.05 $\mu$m pore size filters) |
|---|---|---|---|---|---|
| 1 | 0.580–1.064 | 49.6 | 157.5 | 2.7 | 8.7 |
| 2 | 4.021–4.461 | 48.2 | 173.5 | 2.9 | 10.5 |
| 3 | 8.006–8.628 | 54.7 | 117.9 | 2.3 | 5.1 |
| 4 | 9.228–9.717 | 49.2 | 98.5 | 2.7 | 5.4 |
| 5 | 10.289–10.837 | 47.8 | 137.3 | 2.3 | 6.7 |
| 6 | 10.289–10.837 | 44.7 | 105.3 | 2.2 | 5.1 |
| 7 | 11.369–11.972 | 64.9 | 102.8 | 2.9 | 4.5 |
| 8 | 11.369–11.972 | 54.6 | 117.1 | 2.4 | 5.2 |
| Average | | 51.7 | 126.2 | 2.6 | 6.4 |
| Std. Dev. | | 6.3 | 27.4 | 0.2 | 2.2 |

*The mean number of particles per field of view (10,000× magnification) is denoted $N_F$.
§The mean number of particles generated per cycle is denoted $N_C$.

Example 4
Characterization of Particle Size and Number

Each filter membrane was mounted on an aluminum stub, sputter coated with gold, and examined using a SEM (S360, Leica, Inc., Deerfield, Ill.). Images were taken at a magnification of 10,000× and transferred to a digital imaging system (eXL II, Oxford Instruments, Ltd., England). A minimum of twenty fields of view were analyzed per filter membrane. Particle diameter ($D_p$) was calculated based on the projected area (A) of each particle. This parameter was based on circular geometry and calculated as follows:

$$D_p = 2(A/\pi)^{1/2} \tag{1}$$

For each filter membrane, the mean number of particles per field of view ($N_F$) was determined, and the number of particles generated per cycle of testing ($N_C$) was calculated as follows:

$$N_C = N_F (A_{FILTER}/A_{FIELD}) d/c \quad (2)$$

where $A_{FILTER}$=area of filter membrane=962 mm$^2$; $A_{FIELD}$= area of field of view=9.0×10$^{-5}$ mm$^2$; d=dilution ratio=2500; and c=number of test cycles.

For each type of filter membrane, the data from the different digests were pooled. The particle diameter data were presented as the mean, median, mode, and standard deviation. The number of particles per cycle was presented as the mean and standard deviation. Significant differences (ANOVA; α=0.05) in mean particle parameters were determined between the particles deposited on the 0.2 μm and 0.05 μm pore size filter membranes. The Kruskal-Wallis test was used to determine significant differences in median particle diameter between the two filter membranes.

Example 5
Reproducibility of Particle Isolation Method

For the acid digestion/vacuum filtration method used in this study, a strong linear correlation has been demonstrated between measured wear volume (as determined gravimetrically) and the volume of particles recovered from a total joint simulator (Scott et al., 2000). For digests filtered through a 0.05 μm pore size filter membrane, inter-observer reproducibility has been found to be within 10% of the mean value for each of the following parameters: (i) number of particles generated per cycle of testing; and (ii) mean particle diameter (Table 2).

TABLE 2

Wear Particle Data Demonstrating Interobserver Reproducibility for Two Serum Samples Harvested from a Hip Simulator (Mean ± Std. Dev.).

| Serum Sample | $N_F$* Observer 1 | $N_F$* Observer 2 | Mean Particle Diameter (μm) Observer 1 | Mean Particle Diameter (μm) Observer 2 |
|---|---|---|---|---|
| A | 123.6 ± 20.8 | 123.8 ± 45.0 | 0.11 ± 0.12 | 0.12 ± 0.14 |
| B | 76.3 ± 12.0 | 78.1 ± 21.2 | 0.20 ± 0.29 | 0.22 ± 0.32 |

*The mean number of particles per field of view (10,000× magnification) is denoted $N_F$.

Example 6
Verification of Particle Identity

Fourier transform infrared spectroscopy (FTIR) was performed to determine the identity of wear debris from three of the serum samples. In each case, approximately one mg of particles was transferred from the filter membranes onto a KBr disk and identified using a FTIR spectrometer with an attached infrared microscope (FTS165 spectrometer, UMA250 microscope, Bio-Rad Laboratories, Hercules, Calif.). The FTIR spectra of the particles isolated from serum were compared with that of a commercially available HDPE powder (Shamrock Technologies Inc., Newark, N.J.).

Example 7
Current Wear Particle Procedure Underestimate the Number of Particles Generated by Prosthetic Bearing Components UHMWPE liners were articulated against CoCrMo heads on an anatomic hip simulator up to 12 million cycles. Serum samples were periodically harvested and subjected to a validated acid digestion method Scott et al., 2000). Replicate digests were vacuum filtered through either a 0.2 μm or 0.05 μm pore size filter membrane. Relative differences in the particle number and size distribution were determined for each membrane pore size.

Figure 4:
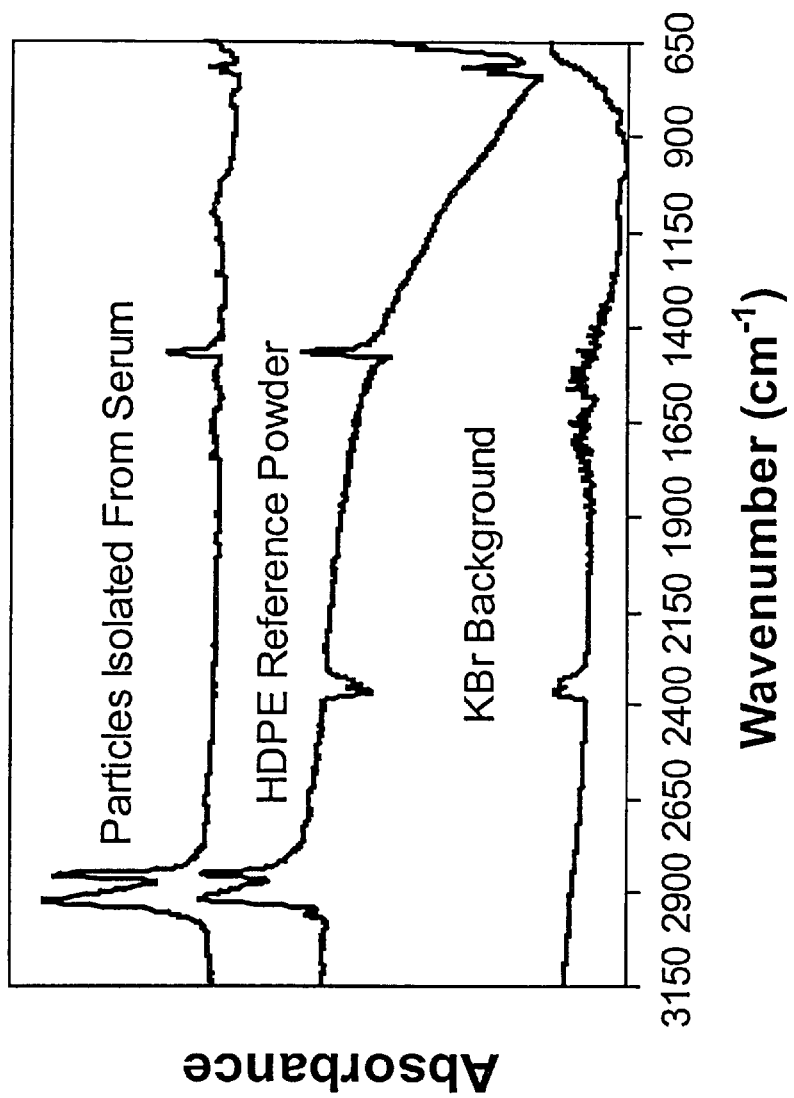
FIG. 4. Fourier transform infrared spectra of particles recovered from serum, HDPE reference material, and the KBr background.

The recovered particles were characterized using Fourier transform infrared spectroscopy (FTIR) and scanning electron microscopy. The FTIR spectra of the particles recovered from the hip simulator sera were similar to that of the reference HDPE material and consistent with UHMWPE in that they had major peaks around 2917, 2850, 1470, and 721 cm$^{-1}$ (FIG. 4) (Painter et al., 1982). Extraneous peaks and valleys were found to correspond with the peak positions of the KBr disk. No evidence of impurities, such as filter material, debris from the tubing through which serum was circulated, or undigested proteins, was found.

Figure 5:
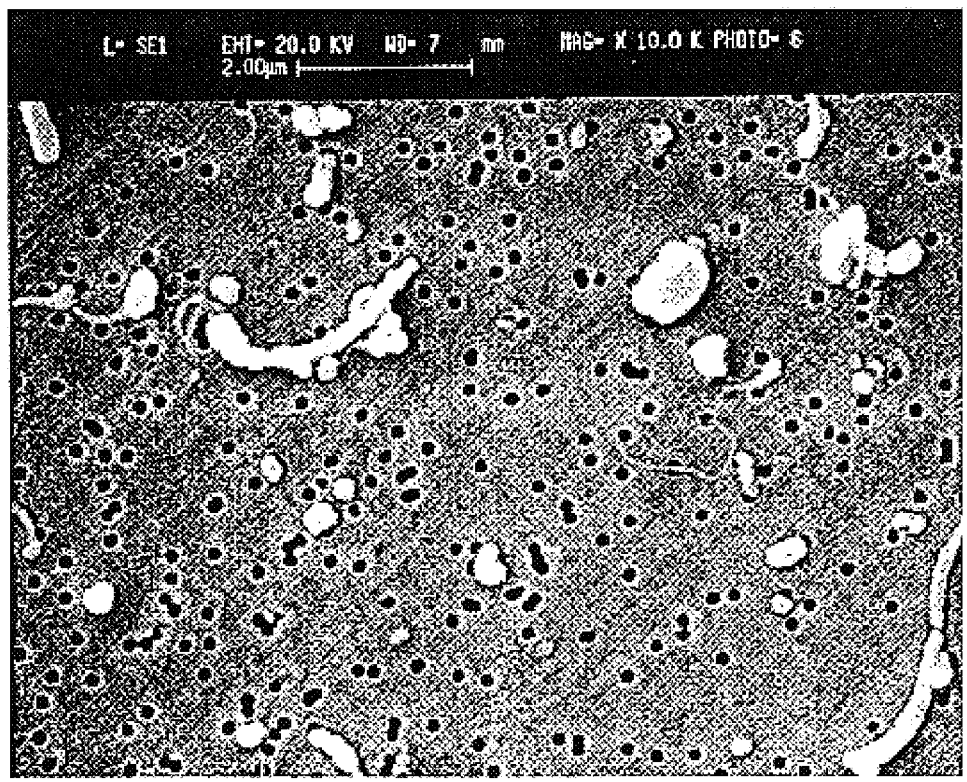
FIG. 5. Scanning electron micrograph of wear debris isolated from hip simulator serum and recovered on a 0.2 $\mu$m pore size filter membrane.
Figure 6:
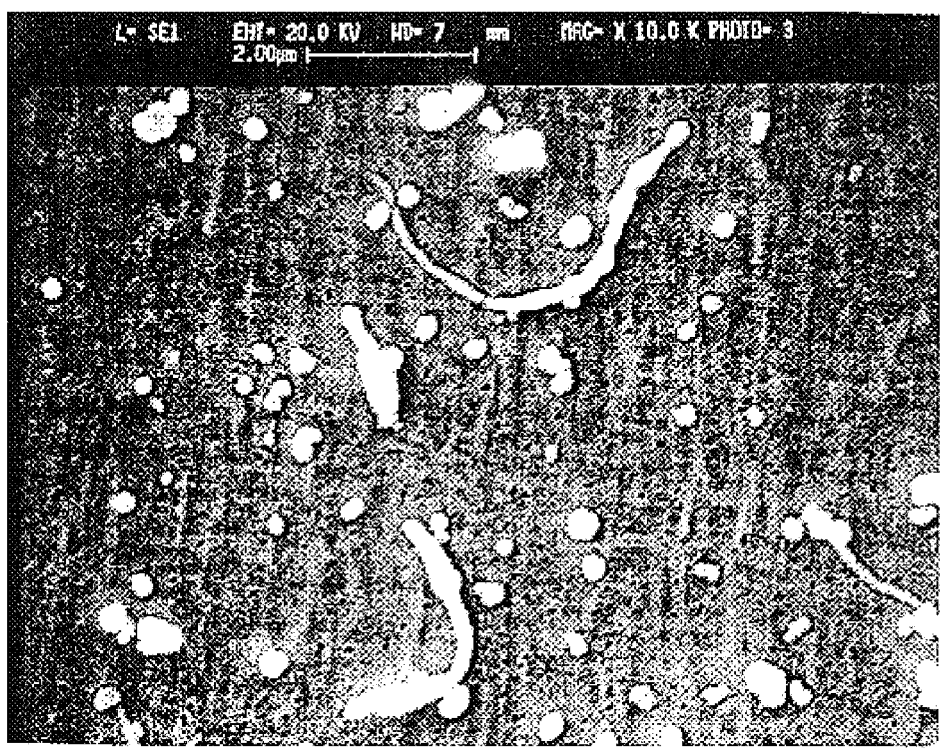
FIG. 6. Scanning electron micrograph of wear debris isolated from hip simulator serum and recovered on a 0.05 $\mu$m pore size filter membrane.
Figure 7:
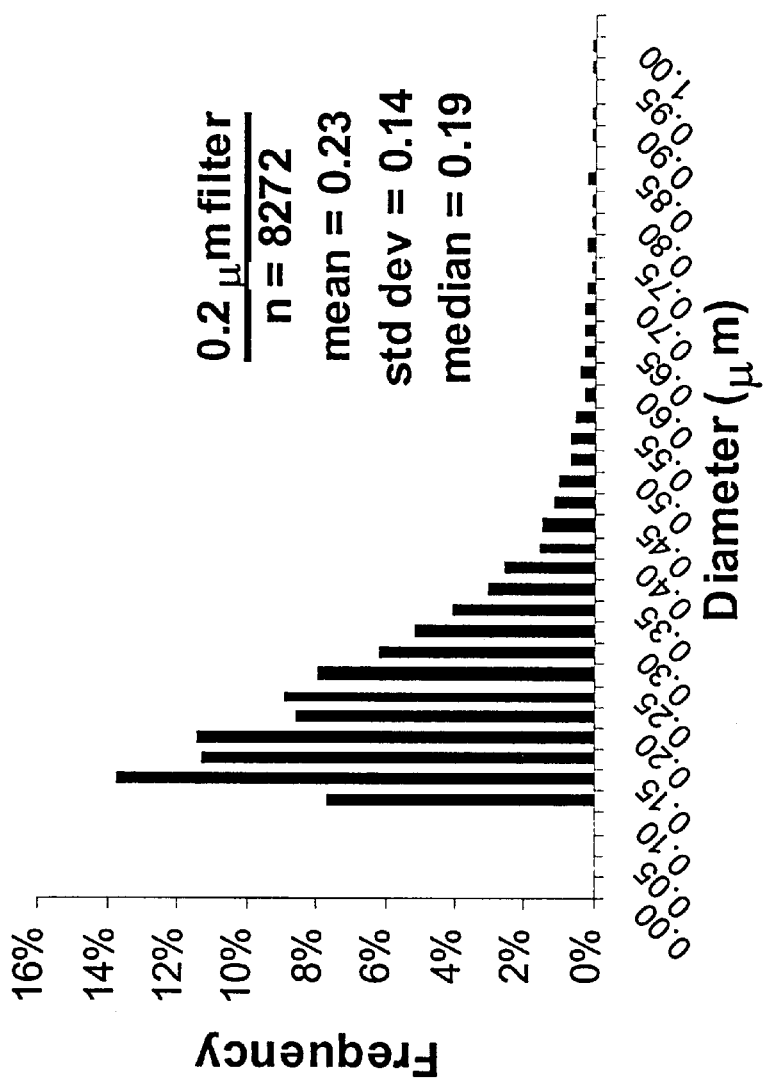
FIG. 7. Size distribution of the particles recovered on the 0.2 $\mu$m pore size filter membranes.
Figure 8:
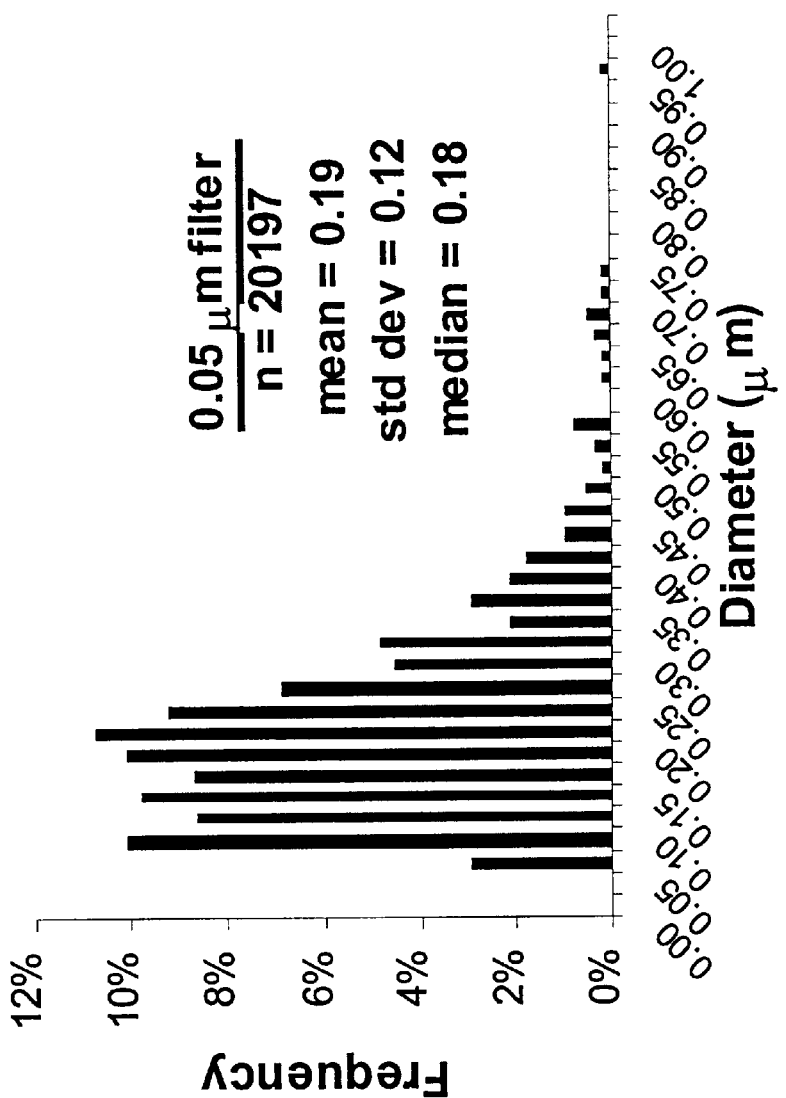
FIG. 8. Size distribution of the particles recovered on the 0.05 $\mu$m filter pore size membranes.

SEM analysis revealed that the recovered wear particles were distributed uniformly on both types of filter membranes (FIGS. 5 and 6). Minimal agglomeration of particles was observed. The wear particles deposited on both the 0.2 μm and 0.05 μm pore size filter membranes were predominantly submicron and round in appearance. Elongated fibrils (3 to 10 μm in length) were occasionally observed on both types of filter membranes. For the data pooled from all eight serum samples, the total numbers of particles imaged on the 0.2 μm and 0.05 μm pore size filters were 8272 and 20197, respectively. The size distributions for the particles deposited on the 0.2 μm and 0.05 μm pore size filters are presented in FIGS. 7 and 8, respectively. The wear particles recovered on the 0.2 μm and 0.05 μm pore size filter membranes were spatially distributed in an uniform manner. Agglomeration of particles was minimal. Because individual particles were clearly discernable from other particles and distributed uniformly on the filter membranes, sampling errors were minimized, leading to a more accurate determination of particle count and size distribution.

For particles isolated on the 0.2 μm pore size filters, the mean (0.23 μm) of the size distribution was above the specified membrane pore size, whereas the median (0.19 μm) was below the specified pore size. The peak (mode) of the distribution occurred well below the 0.2 μm pore size at 0.13 μm. Over half (52.2%) of the total number of particles detected had diameters below the filter pore size of 0.2 μm. For the particles deposited on the 0.05 μm pore size filters, the mean (0.19 μm) and median mean (0.18 μm) diameters were well above the specified membrane pore size. No single dominant peak occurred in the size distribution, with the majority of particles evenly distributed between 0.08 and 0.25 μm. Only 2.8 percent of the total particles detected had diameters below the filter pore size of 0.05 μm. The mean and median diameters of the particles deposited on the 0.05 μm membranes were significantly lower (p<0.001) than those of particles on the 0.2 μm pore size filter.

The 0.05 μm pore size filter membranes contained a greater number of wear particles than the 0.2 μm membranes (Table 1). The mean number of particles generated per cycle was 6.4×10$^6$±2.2×10$^6$ for the serum digests passed through the 0.05 μm pore size filters and was 2.6×10$^6$±0.2×10$^6$ for the digests filtered through the 0.2 μm pore size membranes. This difference was statistically significant (p=0.002).

Figure 9:
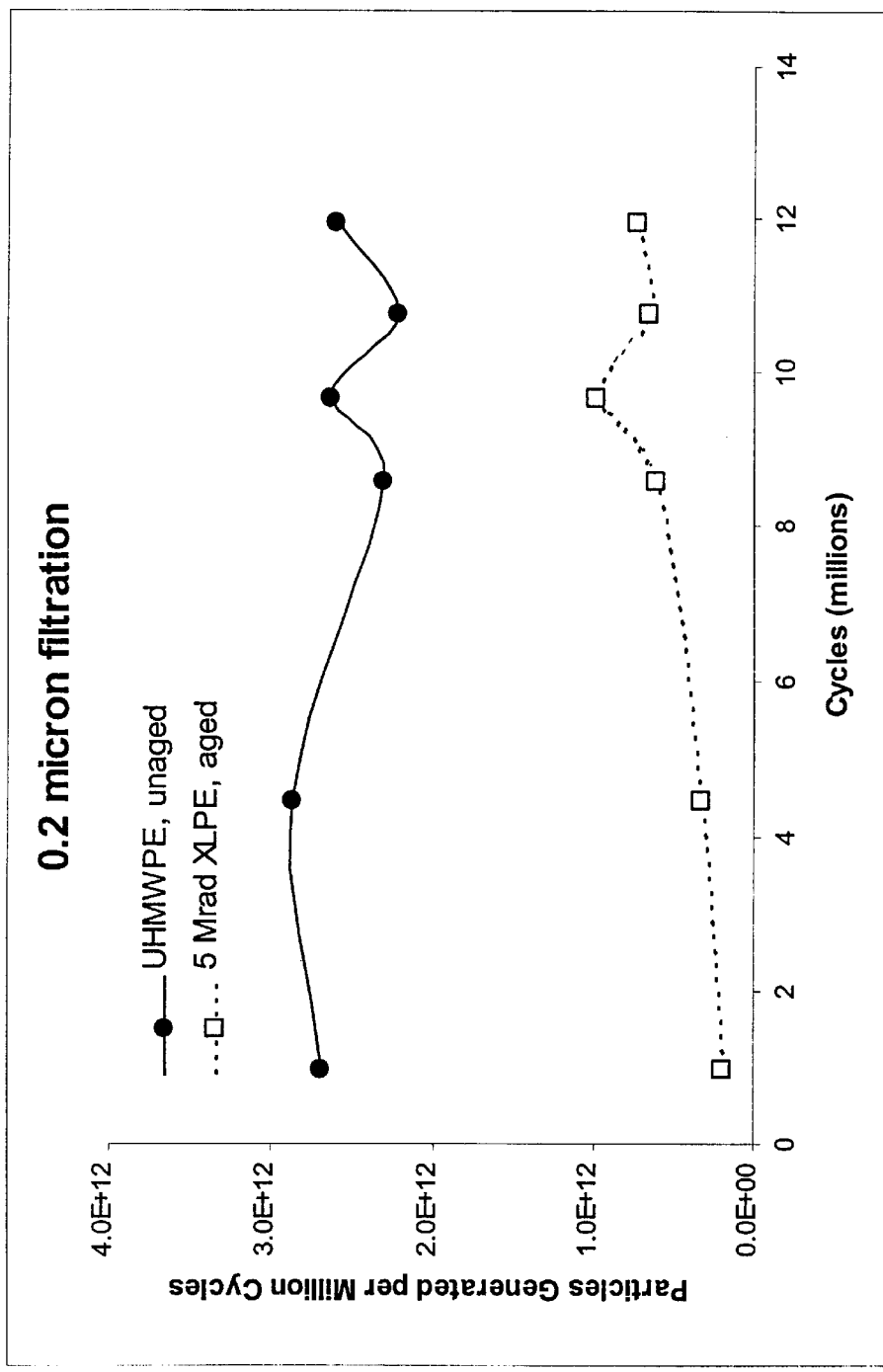
FIG. 9. Particles generated per million cycles using 0.2 $\mu$m filtration.
Figure 10:
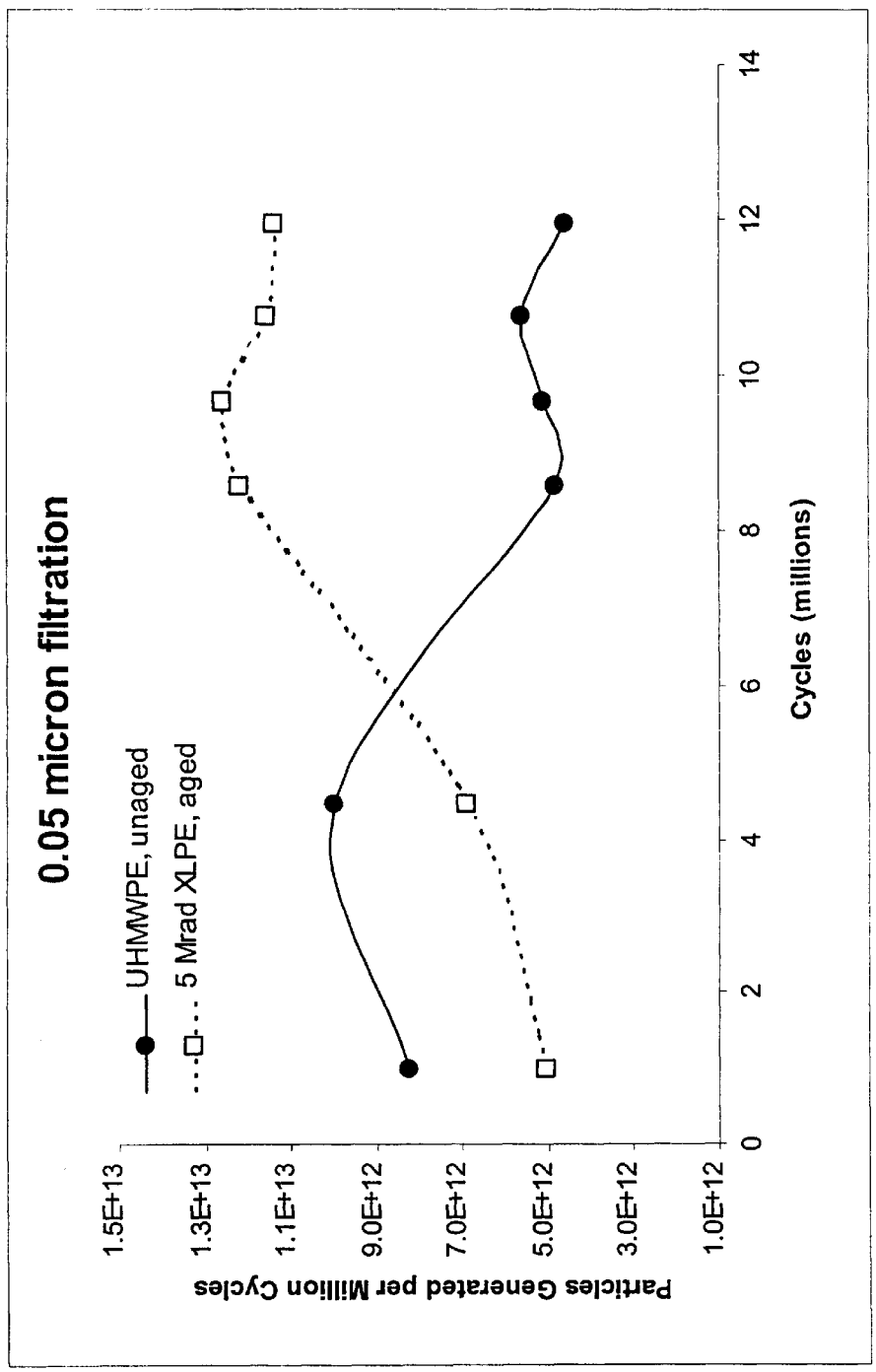
FIG. 10. Particles generated per million cycles using 0.05 $\mu$m filtration.

The use of 0.2 μm pore size membranes caused an underestimate of the number of wear particles generated per million cycles for both conventional and 5 MRad doses of crosslinked UHMWPE (FIG. 9 and FIG. 10).

When vacuum filtration is used to isolate UHMWPE wear debris from digested hip simulator serum, the number and size distribution of recovered particles is strongly dependent upon the pore size of the filter membrane. A substantial number of wear particles passed freely through the pores of the 0.2 μm pore size membranes. Filtering digested serum through a 0.2 μm pore size filter underestimates the number, and consequently the surface area and volume of finer sized particles. A significantly greater number of finer sized particles can be isolated and analyzed by filtering digested serum through a 0.05 μm pore size filters. The entire digestion and filtration procedure took approximately 75 minutes when the digests were filtered through 0.2 μm pore size filter membranes. Filtering the digests through 0.05 μm pore size filter membranes added only 5 minutes to the procedure with no significant increase in the cost of materials and equipment. This increase in procedural time was well justified due to the fact that the number of particles recovered from hip simulator serum, and consequently the size distribution, was strongly dependent upon the pore size of the filter membrane used. Fine wear particles have been found to greatly influence the macrophage response to wear debris. This underscores the importance of using finer pore size (<0.05 μm) filter membranes to isolate and characterize wear debris generated from new orthopaedic bearing materials.

Example 8
Wear Particle Analyses of Conventional and Crosslinked UHMWPE Tested in an Anatomic Hip Simulator Numerous forms of crosslinked UHMWPE, which demonstrate dramatic reductions in hip simulator gravimetric wear, have been developed (McKellop et al., 1999; Muratoglu et al., 1999) and used clinically with the intent to reduce particle-induced osteolysis. It is generally believed that gravimetrically measured reductions in wear translate into reductions in particle generation. The relationship between gravimetric wear volume and wear particle characteristics (size, surface area, and volume) was investigated by the comparison of one conventional and two variations of crosslinked UHMWPE.

Anatomic hip simulator (AMTI, Watertown, Mass.) tests were carried out to 10 million cycles on the following materials: (i) conventional UHMWPE (C-PE), (ii) 5 MRad crosslinked UHMWPE (5-XPE), and (iii) 10 MRad crosslinked UHMWPE (10-XPE). Ram extruded GUR 1050 material (PolyHi Solidur, Ft. Wayne, Ind.) was the starting material for all tests. Crosslinking was carried out at gamma irradiation doses of 5 and 10 MRad (SteriGenics, Gurnee, Ill.), followed by melt annealing (2 hrs at 150° C.) and slow cooling. Acetabular liners (32 mm ID) were machined from bar stock, followed by EtO sterilization. The 5-XPE and 10-XPE liners were artificially aged at 70° C. and 5 atm O2 for 3 weeks prior to testing (Sanford et al, 1995). Hip simulator testing (n=3 for each group) was carried out against 32 mm CoCrMo heads in 100% bovine serum. The testing was interrupted periodically for weight measurements and serum replacement. Wear particles were harvested from test serum using a previously validated acid digestion/vacuum filtration protocol (Scott et al., 2000). The particles deposited on the 0.05-μm pore size filter membranes were characterized under a scanning electron microscope (SEM) at magnifications of 1,000× and 20,000×. A minimum of 20 random, non-overlapping fields and 100 particles were imaged to ensure that the detected particles were representative of the entire particle population within each serum sample. For each material, the mean particle diameter was determined and the following parameters were calculated per million cycles: (i) number of particles, (ii) surface area of particles, and (iii) volume of debrisgenerated. Particle diameter, surface area, and volume were calculated assuming spherical geometry. ANOVA and Duncan's multiple range tests were used to determine significant differences ($\alpha=0.05$) in mean particle diameter, number of particles, surface area of particles, and volume of debris generated between the material conditions.

Figure 11:
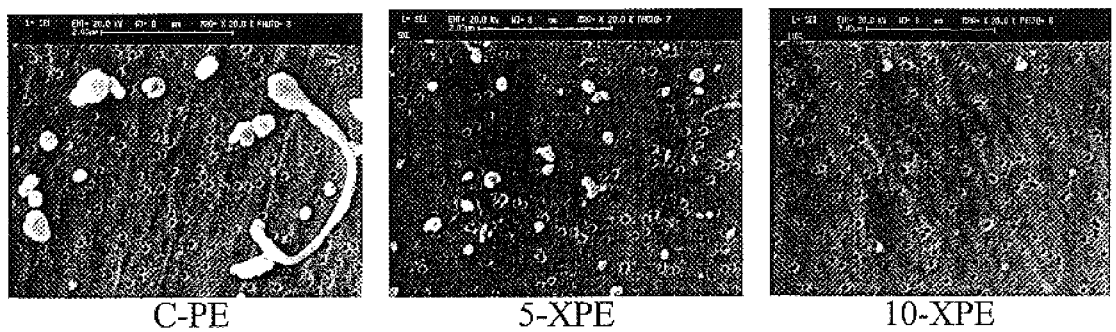
FIG. 11. SEM micrographs of UHMWPE particles extracted from serum

The gravimetric wear rates decreased as the crosslinking radiation dose increased. For the C-PE, the wear rate was 36.9 mg/Mcycles, which decreased to 9.0 mg/Mcycles for the 5-XPE, which further decreased to −1.1 mg/Mcycles for the 110-XPE (Table 3). Based on SEM micrographs, the C-PE particles were predominantly submicron spheroids, with occasional fibrils 5 to 10 μm in length (FIG. 11). The 5-XPE and 10-XPE particles were predominately submicron spheroids (FIG. 11).

In addition to the highest gravimetric wear rate, the C-PE material exhibited the largest particle diameter, surface area, and volume of debris generated (p<0.05 for all combinations of pairs, Table 3). Particle diameter and the surface area and volume of particles decreased with increasing crosslinking radiation dose. The 5-XPE material generated the highest number of particles, resulting in twice the number of particles per Mcycles than C-PE (Table 3). The 10-XPE material generated less than half the number of particles per Mcycle compared to C-PE.

TABLE 3

Gravimetric Wear Rate, Particle Diameter, Surface Area, Volume, and Number for the Tested Materials: Mean ± 95% Confidence Interval

|  | C-PE | 5-XPE | 10-XPE |
|---|---|---|---|
| Gravimetric Wear Rate (mg/Mcycle) | 36.94 ± 0.48 | 9.02 ± 0.55 | −1.11 ± 0.22 |
| Particle Diameter (μm) | 0.206 ± 0.012 | 0.118 ± 0.003 | 0.091 ± 0.003 |
| Particle Surface Area (m²/Mcycle) | 1.17 ± 0.13 | 0.69 ± 0.12 | 0.09 ± 0.02 |
| Particle Volume (mm3/Mcycle) | 95.84 ± 14.69 | 22.45 ± 3.45 | 4.16 ± 1.17 |
| Particle Number per Mcycles (1 × 10$^{12}$) | 5.76 ± 0.96 | 12.05 ± 1.88 | 2.28 ± 0.25 |

Increasing the crosslinking radiation dose resulted in a more wear resistant polyethylene as tested in our anatomic hip simulator, consistent with previous reports (McKellop et al., 1999; Muratoglu et al., 1999). The surface area and volume of particles decreased with increasing radiation dose. Particle size (diameter) also decreased with increasing radiation dose. Due to different particle size distributions, a unique relationship between gravimetric wear and particle number existed for each tested material. As a result, the reduction in gravimetric wear for the 5-XPE material did not translate into a reduction in particle number when compared with the C-PE material.

The mass loss due to wear for the 10-XPE liners was less than the fluid absorption that occurred during testing. As a result, the 10-XPE liners showed a net weight gain. Particle analysis, however, showed that small, but measurable volumes of wear particles were generated. Wear particle analysis may thus provide a more direct measurement of the volume and number of particles generated from highly crosslinked UHMWPE and may be used to supplement gravimetric measurements for low wear materials.

Macrophage response to particulate wear debris is believed to be an important factor in osteolysis. It is well established that the cellular response is dependent upon particle number, size, surface area, and material chemistry, among other factors (Shanbhag et al, 1997; Green et al, 1998; and Gonzalez et al., 1996). Differences in particle number, size, and surface area were observed among conventional and crosslinked UHMWPE. Thus the biological response to the particulate forms of these three materials may differ due to varying particle characteristics.

Example 9
Production of Mediators by Macrophages Exposed to UHMWPE Particles Macrophages are isolated using the method of Green et al., 1998. Human macrophages are co-cultured with conventional UHMWPE, 5 MRad crosslinked UHMWPE, and 10 MRad crosslinked UHMWPE at various concentrations. The particles are added to 1% agarose and poured into plates. Concentrations of particles that are used are 0, 1 ×the amount of particles detected at 1 million cycles, 2×, 5×, and 10×. Lipopolysaccharide is used as a positive control. Macrophages are then added to the top of the plates and incubated at 37° C. for 24 hours. The amount of IL1-α and TNF-α produced by the macrophages at each particle concentration is measured by ELISA. IL1-α is assayed using paired monoclonal antibodies and TNF-α is measured using a modified double antibody sandwich technique.

Example 10
Particle Size Versus Particle Numbers and Volumes for Conventional and Crosslinked UHMWPE Numerous forms of crosslinked UHMWPE have demonstrated dramatic reductions in hip simulator gravimetric wear. (McKellop et al., 1999; Muratoglu et al., 1999; and Essner et al., 2000). While gravimetric techniques provide a measurement of the total mass of debris generated from wear surfaces, no information about individual particles is gained. The objectives of this study were to directly determine the number, size distribution, and volume distributions for UHMWPE particles generated during hip simulator testing. One conventional and two variations of crosslinked UHMWPE were compared in this study.

Anatomic hip simulator (AMTI, Watertown, Mass.) tests were carried out to 15 million cycles on the following materials: (i) conventional UHMWPE (C-PE), (ii) 5 MRad crosslinked UHMWPE (5-XPE), and (iii) 10 MRad crosslinked UHMWPE (10-XPE). Ram extruded GUR 1050 material (PolyHi Solidur, Ft. Wayne, Ind.) was the starting material for all tests. Crosslinking was carried out at gamma irradiation doses of 5 and 10 MRad (SteriGenics, Gurnee, Ill.), followed by melt annealing and slow cooling. Acetabular liners (32 mm ID) were machined from bar stock and EtO sterilized. The 5-XPE and 10-XPE liners were artificially aged at 70° C. and 5 atm $O^2$ for 3 weeks prior to testing (Sanford et al., 1995). Hip simulator testing (n=3 for each group) was carried out against 32 mm CoCrMo heads in 100% bovine serum. The testing was interrupted periodically for gravimetric measurements and serum replacement. Wear particles were harvested from test serum using a previously validated acid digestion/vacuum filtration protocol (Scott et al, 2000). The particles deposited on the 0.05-μm pore size filter membranes were characterized under a scanning electron microscope (SEM) at magnifications of 1,000× and 20,000×. A minimum of 20 random, non-overlapping fields and 100 particles were imaged to ensure that the detected particles were representative of the entire particle population within each serum sample. For each detected particle, an equivalent circular diameter and spherical volume were calculated based the projected area of the particle. For each material condition, the mean number of particles generated per cycle (N) of testing was determined. The following distributions were also plotted: (i) particle number vs. diameter and (ii) total particle volume vs. diameter. Total particle volume was calculated as the sum of individual particle volumes contained within each specified particle diameter interval. ANOVA and Duncan's analyses were used to test for significant differences in particle generation rates between the material conditions.

The gravimetric wear rates decreased as the crosslinking radiation dose increased. For the C-PE, the mean wear rate ±95% CI was 36.9±0.5 mg/Mcycles, which decreased to 9.0±0.6 mg/Mcycles for the 5-XPE, which further decreased to −0.5±0.2 mg/Mcycles for the 10-XPE. Based on SEM micrographs, the C-PE, 5-XPE, and 10-XPE particles had the same predominant morphology—submicron granules (FIG. 11). Fibrils 5 to 10 μm in length were occasionally seen for the C-PE particles (FIG. 11).

The 5-XPE material generated the greatest number of particles per cycle ($N=11.1\times10^6 \pm 2.5\times10^6$), resulting in 78% more particles per cycle than the C-PE material ($N=6.2\times 10^6 \pm 1.1\times10^6$) ($p<0.01$). The 10-XPE liners ($N=2.2\times 10^6 \pm 0.2\times10^6$) generated 65% fewer particles per cycle than the C-PE liners ($p<0.01$).

Figure 12:
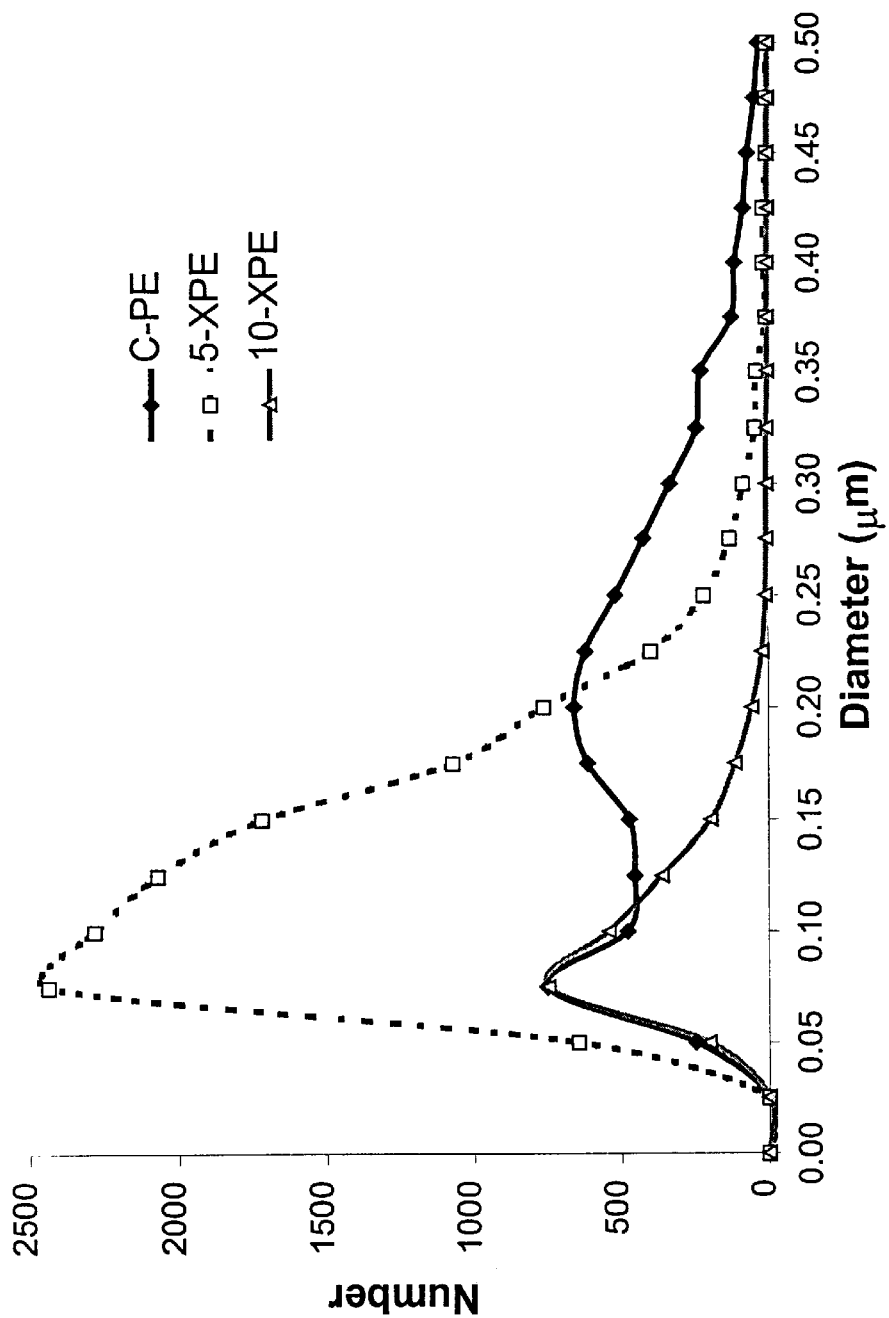
FIG. 12. Particle number vs. size histogram.
Figure 13:
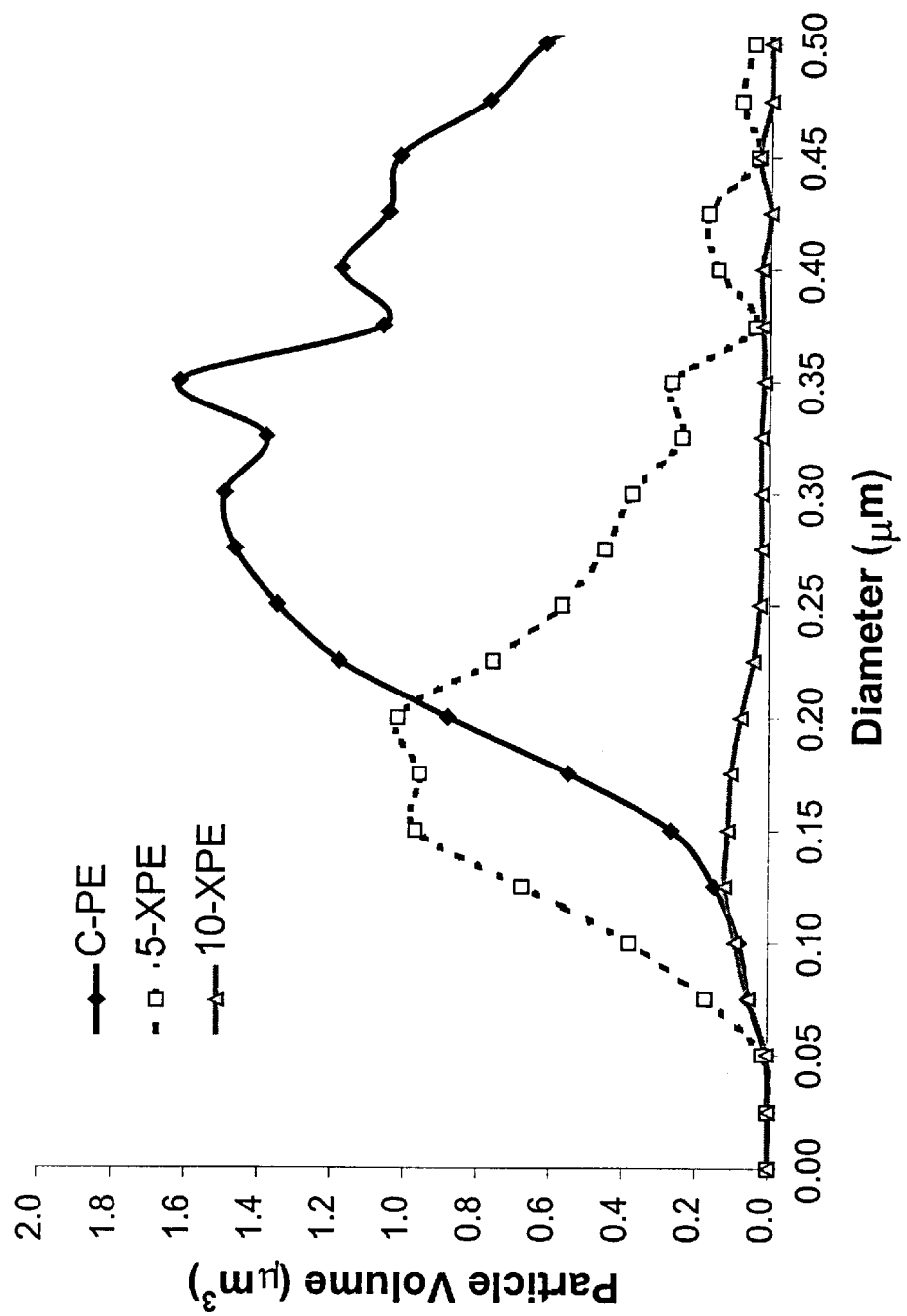
FIG. 13. Particle volume vs. size histogram.

The particle number vs. size distributions for the three material conditions are presented in FIG. 12. The distributions of total particle volume vs. size are presented in FIG. 13. Because the three materials produced different numbers and volumes of particles over the duration of testing, the distributions are presented in absolute number instead of percent frequency. The 5-XPE liners produced a greater number and volume of particles below 0.2 μm in diameter than the C-PE liners. Above 0.2 μm, the C-PE particles were greater in number and volume of than the 5-XPE particles. The C-PE and 10-XPE liners generated an equivalent number and volume of particles with diameters less than 0.125 μm. Above 0.125 μm, the C-PE particles were greater in number and volume than 10-XPE particles.

Increasing the crosslinking radiation dose resulted in lower gravimetric wear as tested in our anatomic hip simulator, consistent with previous reports (McKellop et al., 1999; Muratoglu et al., 1999). Increasing radiation dosage also affected the particle size distribution, resulting in a unique relationship between gravimetric wear and particle number for each tested material. As a result, the reduction in gravimetric wear for the 5-XPE material did not translate into a reduction in particle number when compared with the C-PE material.

In vitro cell culture studies have shown that macrophage response is a function of particle morphology, size, number, and volumetric dose, among other factors (Shanbhag et al., 1997; Green et al, 2000; and Gonzalez et al., 1996). Conventional and two crosslinked UHMWPE materials produced particles that were similar in morphology. However, differences in the particle number and volumetric distributions existed between the three materials. The 5-XPE material generated the greatest number and volume of particles with diameters below 0.2 μm. Above 0.2 μm, the C-PE material generated the greatest number and volume of particles. For every size interval, the number and volume of 10-XPE particles were less than or equal to that of the C-PE particles. A recent cell culture study showed that smaller UHMWPE particles (0.24 μm) produced bone resorbing activity at a lower volumetric dose (10 $\mu m^3$/macrophage), while larger particles (0.45 μm and 1.71 μm) produced bone resorbing activity at doses of 100 $\mu m^3$ per macrophage (Green et al, 2000). Because the particulate forms of the three materials tested have exhibited different particle size distributions, the biological response to wear debris from these materials may differ.

Example 11
Lamellar Thickness

Lamellar thickness values were determined using a TA Instruments 2910 differential scanning calorimeter (DSC). Testing was conducted per ASTM D 3417. Five samples weighing approximately 2.5 mg were taken from the core of the following materials: (i) GUR 1050 UHMWPE barstock that was gamma-irradiated to a dose of 10 MRad and subsequently annealed at 147° C. (XL-147); and (ii) GUR 1050 UHMWPE barstock that was gamma-irradiated to a dose of 10 MRad and subsequently annealed at 140° C. (XL-140).

The samples were crimped into aluminum crucibles and placed in the DSC chamber. The chamber was continuously flushed with nitrogen gas at a flow rate of approximately 30 ml/min. The reference sample was an empty aluminum crucible. A DSC cycle consisted of a 2 minute equilibrating at 30° C. followed by heating to 150° C. at 10° C./min rate.

The temperature corresponding to the peak of the endotherm was taken as the melting point ($T_m$). The lamellar thickness (1) was calculated as follows:

$$l = (2 \cdot \sigma_e \cdot T_m^\circ)/(\Delta H \cdot (T_m^\circ - T_m) \cdot \rho)$$

where $\sigma_e$ is the end free surface energy of polyethylene ($2.22 \times 10^{-6}$ cal/cm$^2$), $\Delta H$ is the heat of melting of polyethylene crystals (69.2 cal/g), p is the density of the crystalline regions (1.005 g/cm$^3$), and $T_m^\circ$ is the melting point of a perfect polyethylene crystal (418.15 K).

The mean lamellar thickness values were 369.0 and 346.9 Angstroms, respectively, for the XL-147 and XL-140 materials (Table 4, Table 5).

TABLE 4

XL-147 (147 degree annealing, 10 MRad XLPE)

| Sample | Melting Temp (deg C.) | lamellar thickness (Angstroms) |
|---|---|---|
| 1 | 138.3 | 398 |
| 2 | 137.4 | 352 |
| 3 | 137.9 | 376 |
| 4 | 137.7 | 365 |
| 5 | 137.5 | 354 |
| avg | 137.8 | 369.0 |
| std dev | 0.4 | 19.1 |

TABLE 5

XL-140 (140 degree annealing, 10 MRad XLPE)

| Sample | Melting Temp (deg C.) | lamellar thickness (Angstroms) |
|---|---|---|
| 1 | 138.07 | 385 |
| 2 | 136.68 | 321 |
| 3 | 136.89 | 329 |
| 4 | 136.72 | 322 |
| 5 | 137.92 | 377 |
|  | 137.26 | 346.9 |
| std dev | 0.68 | 31.5 |

Example 12

Trans-vinylene Index

For polyethylene, the concentration of trans-vinylene units (TVU) has been shown to be linear with absorbed radiation dose at low dose levels (<40 Mrad) (Lyons et al., 1993). The concentration of TVU can therefore be used to determine the level of crosslinking in UHMWPE.

Trans-vinylene concentration was determined for the following materials: (i) GUR 1050 UHMWPE barstock that was gamma-irradiated to a dose of 2.5 MRad and subsequently annealed at 150° C. (Gamma2.5); (ii) GUR 1050 UHMWPE barstock that was gamma-irradiated to a dose of 5 MRad and subsequently annealed at 150° C. (Gamma5); (iii) GUR 1050 UHMWPE barstock that was gamma-irradiated to a dose of 10 MRad and subsequently annealed at 147° C. (Gamma10-147); and (iv) GUR 1050 UHMWPE barstock that was gamma-irradiated to a dose of 10 MRad and subsequently annealed at 140° C. (Gamma10-140). For each material type a rectangular specimen (63.50×12.70× 6.35 mm) was machined, and 200 to 250 μm thick samples were sliced using a sledge microtome and a diamond blade. For each slice, IR spectra were obtained using a Bio-Rad FTS 25 spectrometer equipped with a UMA 500 infrared microscope. The square sampling area for each spectrum was 200 μm$^{2\times200}$ μm$^2$. The trans-vinylene index (TVI) was calculated by normalizing the area under the trans-vinylene vibration at 965 cm$^{-1}$ to that under the 1900 cm$^{-1}$ vibration. The average TVI for each material type was taken as the average of four measurements taken at depths of 0.5, 1.0, 1.5, and 2.0 mm distances from the surface of the specimens.

Figure 14:
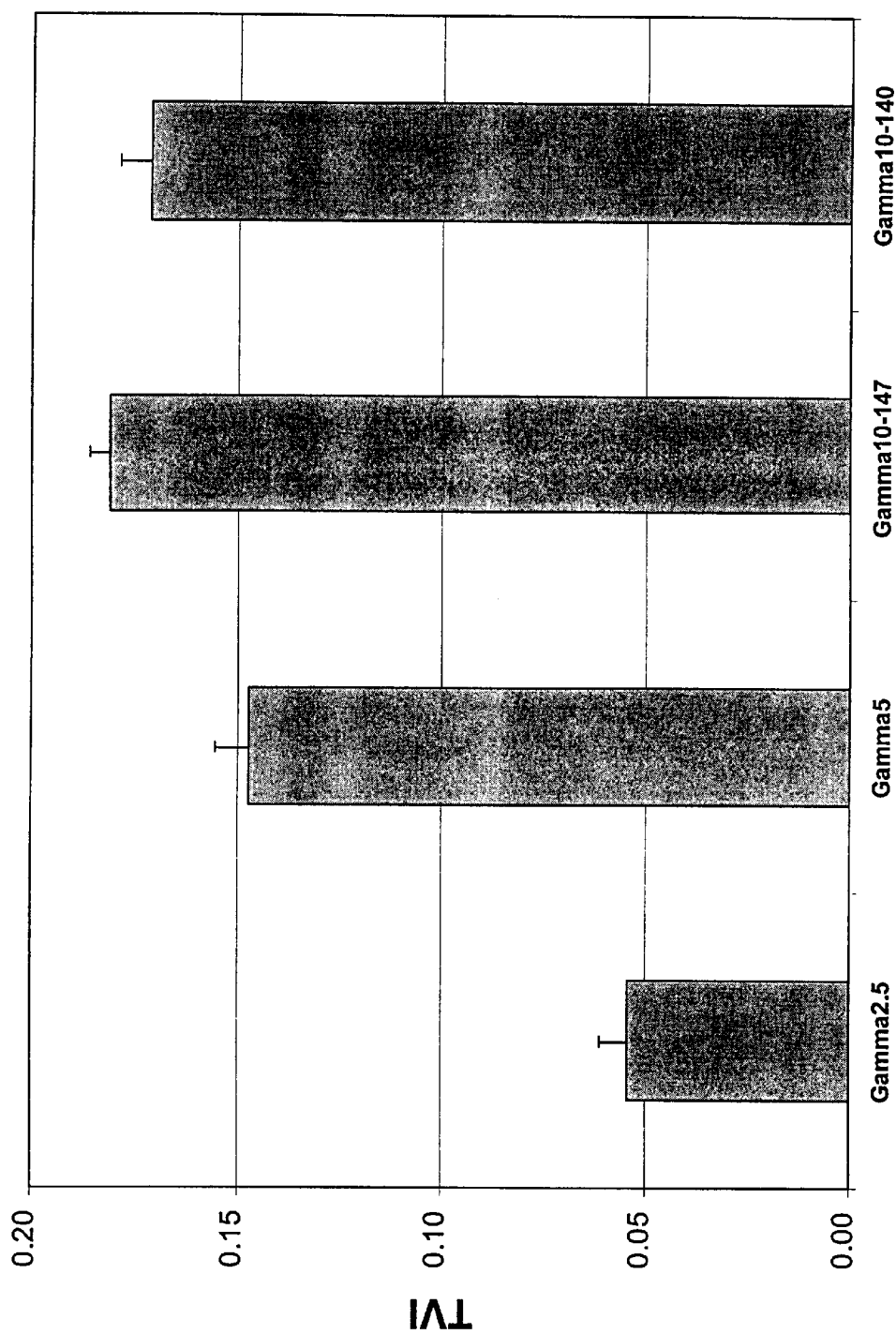
FIG. 14. Trans-vinylene indices for gamma-irradiated and subsequently annealed UHMWPE.

The average TVI values for each material type are shown in FIG. 14. The TVI value was found to increase with increasing radiation dose.

REFERENCES

The following references, to the extent that they provide exemplary procedural or other details supplementary to those set forth herein, are specifically incorporated herein by reference:

U.S. Pat. No. 5,037,938
U.S. Pat. No. 4,055,862
U.S. Pat. No. 4,508,606
U.S. Pat. No. 5,030,402
U.S. Pat. No. 5,037,928
U.S. Pat. No. 5,414,049
U.S. Pat. No. 5,449,745
U.S. Pat. No. 5,543,471
U.S. Pat. No. 5,650,485
U.S. Pat. No. 5,728,748
U.S. Pat. No. 5,879,400
U.S. Pat. No. 6,017,975
U.S. Pat. No. 6,165,220
EP 0722973 A1
EP 0729981 A1
EP 0737481 A1
World Patent Application No. 95/21212
World Patent Application No. 97/29787
World Patent Application No. 97/29793
World Patent Application No. 98/01085
Amstutz, H. C., Campbell, P., Kossovsky, N. and Clarke, I. C. Clinical Orthopaedics and Related Research, 276 (1992) 7–18.
Baker et al., 1999, p. 573.
Bergmann, G., Grachen, R. F. and Rohlmann, A., Journal of Biomechanics, 26 (1993) 969–990.
Bhambri, S., Laurent, M., Campbell, P., Gilbertson, L. and Lin, S. Transactions of the 45$^{th}$ Orthopaedic Research Society, 1999, 838 p.
Bloebaum et al., Clin. Orthop. 269, 120–127, 1991.
Buchanan et al., 1998, Materials Congress 1998, p.148.
Campbell, P., Ma, S., Yeom, B., McKellop, H., Schmalzried, T. P. and Amstutz, H. C. Journal of Biomedical Materials Research, 29 (1995) 127–131.
Chiba, J., Rubash, H. E., Kim, K. J., and Iwaki, Y. Clinical Orthopaedics and Related Research, 300 (1994) 304–312.

Essential Medical Physiology, Johnson, 1992.

Essner, 6th WBC, 854 (2000).

Goldring, S. R., Schiller, A. L. and Roelke, M. Journal of Bone and Joint Surgery, 65A (1983) 575–584.

Gonzalez, J Biomed Mater Res, 30(4), 463–73 (1996)

Gonzalez, JBMR, 30(4), 463–73 (1996).

Gonzalez, O., Smith, R. L., and Goodman, S. B. Journal of Biomedical Materials Research, 30 (1996) 463–73.

Goodman, S. B., Huie, P. Y., Song, Schurman, D., Maloney, W., Woolson, S. and Sibley, R. Journal of Bone and Joint Surgery, 80B (1998) 531–539.

Green, Biomaterials, 19(24), 2297–302 (1998)

Green, JBMR, 53(5), 490–497 (2000).

Green, T. R., Fisher, J., Matthews, J. B., Stone, M. H. and Ingham, E. Journal of Biomedical Materials Research, 53 (2000) 490–497.

Green, T. R., Fisher, J., Stone, M., Wroblewski, B. M. and Ingham, E. Biomaterials, 19 (1998) 2297–2302.

Hamilton, J. V. et al., Trans $43^{rd}$ ORS, 782, 1997.

Hamilton, J. V. et al., Scientific Exhibit, $64^{th}$ AAOS Meeting, February 1997

Harris, W. H. Clinical Orthopaedics and Related Research, 311 (1995) 46–53.

ISO/CD 14242–1.2, "Implants for Surgery—Wear of Total Hip Prostheses—Part I: Loading and Displacment Parameters of Wear Testing Machines and Corresponding Environmental Conditions for Test," Draft Standard, October 1997.

Jasty, M., Bragdon, C., Jiranek, W., Chandler, H., Maloney, W. and Harris, W. H. Clinical Orthopaedics and Related Research, 308 (1994) 111–126.

Jiranek, W. A., Machado, M., Jasty, M., Jevsevar, D., Wolfe, H. J., Goldring, S. R., Goldberg, M. J. and Harris, W. H. Journal of Bone and Joint Surgery, 75A (1993) 863–879.

Johnston, R. C. and Smidt, G. L. Journal of Bone and Joint Surgery, 51A (1969) 1083-1094.

Livingston et al., Trans. ORS, 22, 141–24, 1997.

Lyons, B. J. and Johnson, W. C., Radiolytic Formation and Decay of trans-Vinylene Unsaturation in Polyethylene, in Irradiation of Polymeric Materials: Processes, Mechanisms, and Applications, E. Reichmanis, C. W. Frank, and J. H. O'Donnell, Editors. 1993, American Chemical Society: Washington, D.C., p. 62–73.

Matthews et al., 2000 Biomaterials, p. 2033.

McKellop, CORR, 311, 3–20 (1995).

McKellop, H. A., Campbell, P., Park, S. H., Schmalzried, T. P., Grigoris, P., Amstutz, H. C. and Sarmiento, A. Clinical Orthopaedics and Related Research, 311 (1995) 3–20.

McKellop, J Ortho Res, 17(2)? 157–67 (1999)

Muratoglu, $45^{th}$ ORS Trans, 829 (1999)

Nicdzwiecki, S., Short, J., Jani, S., Sauer, W., Klapperich, C., Ries, M. and Pruitt, L. Transactions of the $25^{th}$ Society for Biomaterials, 1999, 150 p.

Niedzwiecki, SFB Trans., 150 (1998).

Oka, M. et al., "Wear-resistant properties of newly improved UHMWPE," Trans. $5^{th}$ World Biomaterials Congress, 520, 1996.

Oonishi, H. et al., J. Mat. Sci: Materials in Medicine, 8, 11–18, 1997.

Oonishi, H. et al., Mat. Sci: Materials in Medicine, 7, 753–63, 1966.

Oonishi, H. et al., Radiat. Phys. Chem., 39(6), 495, 1992.

Painter, P. C., Coleman, M. M. and. Koenig, J. L The Theory of Vibrational Spectroscopy and Its Application to Polymeric Materials, John Wiley, New York, 1982, 252 p.

Pathology, Rubin, Second Ed. 1994

Polineni, V. K. et al., J. $44^{th}$ Annual ORS, 49, 1998.

Rose, R. M., Goldfarb, E. V., Ellis, E., and Crugnola, A. N., "Radiation sterilization and the wear rate of polyethylene," Journal of Orthopaedic Research, Vol. 2, No. 4, pp. 393–400, 1984.

Sanford, ORS Trans, 119 (1995)

Schmalzried, T. P., Jasty, M. and Harris, W. H. Journal of Bone and Joint Surgery, 74A (1992) 849–863.

Scott, M., Forster, H., Jani, S., Vadodaria, K., Sauer, W. and Anthony, M. Transactions of the Sixth World Biomaterials Congress, 2000, 1777.

Shanbhag, A. S., Jacobs, J. J., Black, J., Galante, J. O. and Giant, T. T. Journal of Biomedical Materials Research, (1994) 28 81–90.

Shanbhag, A. S., Jacobs, J. J., Giant, T. T., Gilbert, J. L., Black, J. and Galante, J. O. Journal of Bone and Joint Surgery, 76B (1994) 60–67.

Shanbhag, (1997) Clin Ortho, 342, 205–17.

Streicher, R. M., "Influence of Ionizing Irradiation in Air and Nitrogen for Sterilization of Surgical Grade Polyethylene for Implants,: Radiation Physics and Chemistry; The International Journal for Radiation Reactions, Processes and Industrial Applications, Vol. 31, No. 4–6, pp. 693–698, 1988.

Willert, H. G., Bertram, H. and Buchhorn, G. H. Clinical Orthopaedics and Related Research, 258 (1990) 95–107.

Yamamoto et al., Trans. $6^{th}$ World Biomaterials Congress, 485, 2000.

We claim:

1. A medical implant comprising UHMWPE for use in a body, said UHMWPE produced by the process comprising:

crosslinking the UHMWPE;

annealing the UHMWPE;

machining the UHMWPE to form said medical implant;

wear testing the implant;

analyzing wear particles created by said step of wear testing, said step of analyzing having sufficient sensitivity to detect particles having sizes of 0.05 µm or less;

determining the number of particulate debris; and selecting a crosslinking radiation dose that exhibits the lowest number of particulate debris relative to that exhibited by non-crosslinked UHMWPE treated by all of the above steps except said crosslinking step and said selecting step, and wherein the wear particles are decreased to a particle number of less than that exhibited by non-crosslinked UHMWPE treated by all of the above steps except said crosslinking step and said selecting step.

2. The implant of claim 1 wherein said crosslinking is performed using electromagnetic radiation or energetic subatomic particles.

3. The implant of claim 2 wherein said crosslinking is performed using gamma radiation.

4. The implant of claim 2 wherein said crosslinking is performed using e-beam radiation.

5. The implant of claim 2 wherein said crosslinking is performed using x-ray radiation.

6. The implant of claim 1 wherein said crosslinking is performed using chemical crosslinking.

7. The implant of claim 1 wherein said crosslinking is at a dose of greater than five but less than or equal to fifteen MRad.

8. The implant of claim 1 wherein said annealing is performed in the melt stage, in an inert environment, or in an ambient environment.

9. The implant of claim 1 wherein said annealing is performed below or equal to 150° C.

10. The implant of claim 9 wherein the crosslinking is sufficient to form an implant with a trans-vinylene index of greater than or equal to 0.10.

11. The implant of claim 9 wherein the crosslinking is sufficient to form an implant with a trans-vinylene index of greater than about 0.15 and less than about 0.20.

12. The implant of claim 1 wherein said step of analyzing comprises filtering the wear particles through a filter having a pore size of 0.05 $\mu$m or less.

13. The implant of claim 1 wherein said step of analyzing comprises analyzing with a scanning electron microscope.

14. The implant of claim 1 wherein said step of analyzing comprises analyzing with a Fourier Transform Infrared Spectrometer.

15. The implant of claim 1 wherein said step of analyzing comprises analyzing with an automated particle size counter.

16. A medical implant comprising UHMWPE for use in a body, said UHMWPE produced by the process comprising:

crosslinking the UHMWPE;

annealing the UHMWPE;

machining the UHMWPE to form said medical implant;

wear testing the implant;

analyzing wear particles created by said step of wear testing, said step of analyzing having sufficient sensitivity to detect particles having sizes of less than 0.2 $\mu$m;

determining the number of particulate debris; and selecting a crosslinking radiation dose that exhibits the lowest number of particulate debris relative to that exhibited by non-crosslinked UHMWPE treated by all of the above steps except said crosslinking step and said selecting step, and wherein the wear particles are decreased to a particle number of less than that exhibited by non-crosslinked UHMWPE treated by all of the above steps except said crosslinking step and said selecting step.

* * * * *